(12) United States Patent
Hussain et al.

(10) Patent No.: US 8,455,523 B2
(45) Date of Patent: Jun. 4, 2013

(54) COMPOSITIONS AND METHODS FOR TREATING HYPERLIPIDEMIAS

(75) Inventors: M. Mahmood Hussain, Woodbury, NY (US); Jahangir Igbal, Jersey City, NJ (US); Joby Josekutty, Brooklyn, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 12/930,532

(22) Filed: Jan. 7, 2011

(65) Prior Publication Data

US 2012/0029028 A1    Feb. 2, 2012

Related U.S. Application Data

(60) Provisional application No. 61/292,992, filed on Jan. 7, 2010.

(51) Int. Cl.
  *A61K 31/44* (2006.01)
  *A61K 31/195* (2006.01)
(52) U.S. Cl.
  USPC .......................................... 514/342; 514/562
(58) Field of Classification Search
  USPC .................................................. 514/342, 562
  See application file for complete search history.

(56) References Cited

U.S. PATENT DOCUMENTS

2011/0217293 A1* 9/2011 Fujise et al. ............... 424/133.1

* cited by examiner

*Primary Examiner* — Raymond Henley, III
(74) *Attorney, Agent, or Firm* — Dilworth & Barrese, LLP

(57) ABSTRACT

The present invention is directed to a composition and method for the treatment of hyperlipidemias by targeting Microsomal triglyceride transfer protein (MTP). In particular, the present invention is directed to a combination of at least one MTP inhibitor and at least one lipid-lowering agent, both in an amount effective to treat hyperlipidemias.

10 Claims, 24 Drawing Sheets

COMPOSITIONS AND METHODS FOR TREATING HYPERLIPIDEMIAS

CROSS REFERENCE TO RELATED APPLICATIONS

The present application claims the benefit of priority under 35 U.S.C. §119(e) of U.S. Provisional Application No. 61/292,992, filed Jan. 7, 2010.

GOVERNMENT RIGHTS

This invention was funded, at least in part, under grants from the National Institutes of Health: NIH DK-46700. The Government may therefore have certain rights in the invention.

BACKGROUND OF THE INVENTION

High plasma lipids and lipoproteins are risk factors for various cardiovascular and metabolic disorders. Statins enhance the removal of apolipoprotein B (apoB)-lipoproteins and lower plasma cholesterol. Another approach to lower plasma lipids is to inhibit the biosynthesis of apoB-lipoproteins, a process critically dependent on an endoplasmic reticulum (ER) resident chaperone, microsomal triglyceride transfer protein (MTP). MTP inhibitors decrease apoB-lipoprotein secretion and lower plasma cholesterol. However, they increase plasma aminotransferases, such as ALT and AST, indicating liver injury. Therefore, what is needed is an improved method for treating high plasma lipids and lipoproteins increases in microsomal free cholesterol, without causing an increase in induction of Endoplasmic Reticulum stress and cell death.

An estimated 35.4 million Americans in the United States aged 20 or over have total blood cholesterol levels of >240 mg/dl (normal <200 mg/dl). Hyperlipidemic states (total blood cholesterol >200 mg/dl; LDL Cholesterol >100 mg/dl) have been implicated as a major risk factor for cardiovascular disease (CVD), the leading cause of death in the United States for the past 80 years. Numerous clinical trials and outcome studies have demonstrated that improving such dyslipidemia lowers the progression of atherosclerosis as well as the resulting adverse cardiovascular (CV) events. Statins that remove apolipoprotein B (apoB)-containing lipoproteins from plasma have long been the cornerstone of lowering plasma cholesterol.

Despite their acclaim as the "miracle drug", approximately 60% of statin-treated patients continue to have adverse coronary events. Furthermore, many patients cannot achieve current target levels for cholesterol owing either to intolerance or an inadequate response to conventional statin therapy. Increasing dosage of statins to try and reach target levels result in an increased likelihood of encountering statin related side effects such as, rhabdomyolysis. Therefore, there is a need to formulate new approaches or regimens to treat hyperlipidemia. One possible approach is to lower plasma lipids at the stage of lipoprotein biosynthesis. Lipoprotein biosynthesis depends on the carrier protein, apolipoprotein B (apoB), and the chaperone, microsomal triglyceride transfer protein (MTP). MTP transfers triglycerides, phospholipids and cholesterol esters to nascent apoB, which readies the protein for secretion as either a chylomicron from the intestine or as VLDL from the liver.

The present invention is directed to a therapeutic combination and a method for lowering the high plasma lipids and lipoproteins in the blood of a patient without the negative effects of many of the existing drugs/procedures available on the market today.

SUMMARY OF THE INVENTION

The present invention provides a combination comprising at least one Microsomal Triglyceride transfer Protein (MTP) inhibitor and at least one lipid lowering agent, both in an amount effective to treat hyperlipidemias.

It has been surprisingly found that administering this combination avoids increases in plasma AST/ALT, hepatic triglyceride/free cholesterol, and ER stress. Accordingly, the composition and method of the present invention provide a way to treat hyperlipidemias without evidence of hepatic disease by using MTP antagonists along with agents that avoid accumulation of cellular lipids.

Examples of lipid lowering agent include PPARα/PPARγ agonists or statins. An example of a PPARα/PPARγ agonist is (RS)-5-(4-[2-(5-ethylpyridin-2-yl)ethoxy]benzyl)thiazolidine-2,4-dione. An examples of a statin is 1S,3R,7S,8S,8aR)-8-{2-[(2R,4R)-4-hydroxy-6-oxooxan-2-yl]ethyl}-3,7-dimethyl-1,2,3,7,8,8a-hexahydronaphthalen-1-yl (2S)-2-methylbutanoate.

Also provided is a method of treating hyperlipidemias in a subject by administering a combination of at least one Microsomal Triglyceride transfer Protein (MTP) inhibitor and at least one lipid lowering agent to said subject. Preferably, the MTP inhibitor is administered in an amount of about 50-100 mg per day and the lipid-lowering agent is administered in an amount of about 50-100 mg per day. The MTP inhibitor and the lipid lowering agent may be administered together as a pharmaceutical composition or as part of the same, unitary dosage form. The MTP inhibitor and the lipid lowering agent may also be administered separately, but as part of the same therapeutic regimen.

DETAILED DESCRIPTION OF THE INVENTION

Microsomal Triglyceride Transfer Protein (MTP)

Abetalipoproteinemia is characterized by the absence of plasma apoB-lipoproteins, extremely low plasma cholesterol, and lipid soluble vitamin deficiencies. Using genetic approaches it has been shown that afflicted individuals have mutations in the mttp gene. Several mutations in the mttp gene have since been documented in abetalipoproteinemia. Reconstitution of MTP activity in heterologous systems rescued apoB secretion, while tissue specific liver knockout models recreated the apoB and lipid deficiencies present in abetalipoproteinemia. Furthermore, cell culture studies showed that wild type MTP can rescue apoB secretion but mutated proteins cannot. MTP is required during the early stages of assembly to prevent the aberrant folding of apoB and its degradation by proteasomes.

Figure 3:
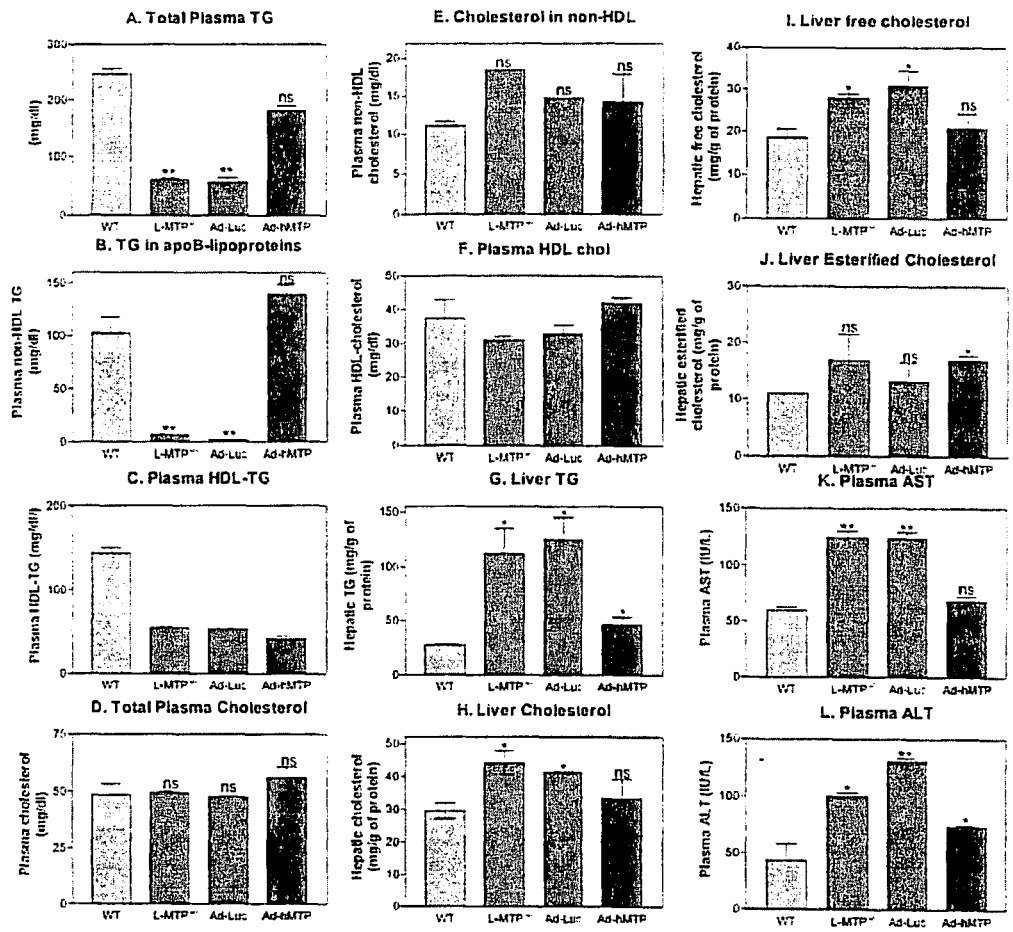
FIG. 3. Effect of hepatic MTP ablation an re-expression on plasma and liver lipids and plasma hepatic enzymes: the hepatic MTP deficient mice (L-MTP$^{-/-}$) were injected with adenoviruses expressing luciferase (Ad-Luc) or human MTP (Ad-hMTP). After 72 h, plasma and tissues were collected for lipid and hepatic enzyme analysis. N+4 each group. L-MTP$^{-/-}$ mice were compared with WT mice. Ad-Luc and Ad-hMTP mice were compared with L-MTP$^{-/-}$ mice. *, $p<0.05$; $p$, 0.01; *, $p<0.001$.

MTP consists of two polypeptides, a 97 kDa MTP subunit and a 55 kDa PDI subunit. The PDI (protein disulfide isomerase) subunit is ubiquitously expressed ER resident enzyme. Based on sequence homology with lipovitellin, the MTP subunit is proposed to contain three domains (FIG. 3); N-terminal β-barrel (green), central α-helical domain (cyan), and C-terminal lipid-transfer (red and blue) cavity. Several independent approaches led to the conclusion that the lipid transfer activity of the MTP is essential for the apoB-lipoprotein assembly and secretion.

MTP can transfer several lipids in vitro. In order to study the importance of different lipid transfer activities of MTP, a *Drosophila* homolog of human MTP was cloned. The *Drosophila* MTP transferred phospholipids but did not transfer triacylglycerols. Even though it lacked the neutral lipid transfer activity, the *Drosophila* MTP was able to assist in the secretion of apoB-lipoproteins indicating that the phospholipid transfer activity was the most ancient activity of MTP and that this activity was sufficient to support apoB-lipoprotein assembly. The phospholipid transfer activity of MTP is also necessary for the lipidation during the biosynthesis of CD1d, a glycolipid antigen-presenting molecule, and in the NKT cell development. We have proposed that phospholipid and triglyceride transfer activities of MTP play different roles during the first step lipidation of nascent apoB. The triglyceride transfer activity may enhance "nucleation" sites for the assembly of apoB-lipoproteins on the ER membrane. The phospholipid transfer activity may play a critical role by adding phospholipids and completing the synthesis of newly detached "primordial" lipoprotein particles and rendering them secretion competent.

MTP in Cholesteryl Ester Biosynthesis

Apart from its lipid transfer activity, we have recently shown that MTP also regulates cholesteryl ester biosynthesis in the liver and intestinal cells. Genetic deletion and chemical inhibition of MTP causes accumulation of cellular triglycerides. It has been assumed that cells would also accumulate cholesteryl esters along with triglycerides. However, we found that inhibition or loss of MTP decreased cellular cholesteryl esters and increased free cholesterol levels. Mechanistic studies revealed that MTP relieves product inhibition of cholesteryl ester synthesis and enhances their biosynthesis.

Increases in cellular free cholesterol might cause tissue damage and enhance the release of hepatic enzymes into the plasma. It is known that high cellular free cholesterol levels damage extra-hepatic tissues. For example, excess amounts of cellular free cholesterol induce apoptosis, especially in the arterial wall macrophages contributing to atherogenesis. Enhanced free cholesterol levels in the ER of macrophages induce ER stress and apoptosis. On the contrary, hepatic free cholesterol is not usually considered a problem since liver can either excrete it as such or after its conversion to bile acids. This assumption may not be totally true. The success of statin therapy is due to the inhibition of hepatic HMG CoA reductase (HMGR) activity present in the ER membranes. Therefore, a more plausible explanation is that free cholesterol in the ER membrane is critical and perturbations that lead to increases in microsomal free cholesterol may cause injury. Furthermore, it has been suggested that the progression of hepatosteatosis to steatohepatitis might be related to free cholesterol, not free fatty acid or triglyceride, accumulation in the liver. The relationship between free microsomal cholesterol assimilation, MTP inhibition, and increases in plasma transaminases can be evaluated by lowering cellular free cholesterol.

A feasible approach to lower cellular cholesterol might be to inhibit HMG CoA reductase. Statins inhibit HMG CoA reductase, increase hepatic LDL receptor expression, and decrease plasma cholesterol. Therefore, it is tempting to suggest that a combined inhibition of MTP and HMG CoA reductase may be useful in lowering plasma cholesterol and avoiding cellular cholesterol accumulation. Similarly, potent inhibitors of squalene synthase can be used with MTP inhibitors to achieve these goals.

Another combinatorial approach to avoid free cholesterol accumulation is to enhance its efflux. In this regards, liver X receptor (LXR) agonists appear promising. LXRs are nuclear hormone receptors that control expression of genes involved in cholesterol efflux in macrophages, hepatic bile acid synthesis, and intestinal cholesterol absorption. LXR agonists increase expression of ABCA1 in macrophages, enhance cholesterol efflux, and decrease atherosclerosis in apoe$^{-/-}$ and ldlr$^{-/-}$ mice. They increase hepatic bile acid synthesis and reduce hepatic cholesterol levels. These agonists up regulate ABCG5 and ABCG8 in the intestine and reduce cholesterol absorption. Unfortunately, a major side effect of LXR agonist is hypertriglyceridemia. MTP inhibitors reduce hypertriglyceridemia. Therefore, it is worth examining whether LXR agonist and MTP antagonists can be used in combination to prevent hypertriglyceridemia, increases in plasma transaminases, and steatosis.

Several animal studies also indicate a relationship between decreased MTP expression and steatosis. Chronic alcohol feeding causes fatty liver and is associated with decreases MTP. Transgenic expression of Hepatitis C virus core protein inhibits MTP activity, reduces VLDL secretion, and causes steatosis. We have shown that steatosis induced by carbon tetrachloride rapidly involves post-translational degradation of MTP. Similarly, inhibition of MTP in cells also results in triglyceride accumulation. Therefore, significant reduction in MTP activity is usually associated with steatosis.

MTP and Steatosis:

There are several reports in humans indicating cellular fat accumulation (steatosis) with decreased MTP expression. Intestinal steatosis is uniformly observed in all abetalipoproteinemia patients. Hepatic steatosis has also been reported with MTP deficiency. An abetalipoproteinemia infant with substantial hepatomegaly and persistent elevated levels of serum aminotransferases but normal bilirubin levels was described in the literature. Microscopic examination revealed large fat droplets in hepatocytes. In addition to genetic defects, there is an association between low MTP expression due to a polymorphism in the promoter sequence and liver steatosis in type 2 diabetes patients. Hepatitis C virus type 3 infected subjects show reduced MTP activity and mRNA levels and high degree of steatosis.

Inhibitors of MTP have been sought as possible treatment options for hyperlipidemia. However, uses of these inhibitors have demonstrated increases in hepatic fat and the plasma transaminases, Alanine Aminotransferase (ALT) and Aspartate Aminotransferase (AST). Our lab has demonstrated that inhibition of MTP results in elevations in hepatic triglycerides and free cholesterol. It has been illustrated in non-hepatic tissue that cellular free cholesterol has damaging effects e.g., an excess amount of cellular free cholesterol induces apoptosis of arterial wall macrophages contributing to atherosclerotic plaque formation. In these tissue macrophages, the elevated free cholesterol localizes to the ER and induces the Endoplasmic Reticulum stress (ER stress) pathway to either maintain survival or signal apoptosis. Free cholesterol is not normally considered a problem in the liver due to the many metabolic pathways in which the organ can deal with free cholesterol; (1) it can be converted into cholesterol esters and secreted with VLDL particles via MTP, (2) it can be converted into bile acids and secreted into the bile canaliculus or (3) it can be effluxed out of the hepatocyte. However, with loss of MTP the ability of the liver to cycle free cholesterol into the esterification pathway diminishes. As a result, accumulation of free cholesterol ensues and may be too great for the liver to compensate with other arms of the cholesterol metabolic pathway. With this in mind, a plausible explanation for plasma transaminase elevation. In the present study we will establish that loss of hepatic MTP results in elevations in cellular free cholesterol and plasma ALT/AST. It is also demonstrated that by alleviating free cholesterol accumulation in the liver, we can lower plasma ALT/AST elevations due to loss of MTP can be lowered. It is shown that the induction of ER stress in the liver as a result of MTP inhibition and that by lowering free cholesterol ER stress can be alleviated. Finally, we will demonstrate that induction of ER stress in the liver can lead to plasma AST/ALT elevations in MTP deficient models and that by inhibiting ER stress we can abrogate or curb the rise in AST/ALT seen with MTP inhibition.

Accordingly, MTP is a possible therapeutic target in treating hyperlipidemias; but its inhibition is associated with side effects. Lowering cellular free cholesterol and inhibiting endoplasmic reticulum (ER) stress avoid toxicities associated with the inhibition of Microsomal Triglyceride Transfer Protein (MTP).

In the development of the present invention it has been found that the genetic ablation of MTP in Reversa mice and its chemical inhibition in western diet fed C57Bl/6J mice decreased plasma triglyceride and cholesterol by 50% and increased hepatic triglyceride by 2-fold consistent with other studies. These mice, however, had 50% increased hepatic free cholesterol and 2 to 3-fold higher plasma AST/ALT. Daily administration of PPARα/PPARγ agonists to MTP ablated or inhibited mice reduced hepatic triglyceride/free cholesterol and avoided increases in plasma AST/ALT. Lovastatin reduced hepatic free cholesterol without affecting triglyceride and abrogated increases in plasma AST/ALT. Therefore, implying that increases in plasma AST/ALT were most likely due to increases in hepatic free cholesterol. Mechanistic studies showed that MTP inhibition and hepatic free cholesterol accumulation increase hepatic ER stress. Inhibition of ER stress with 4-phenyl butyric acid did not reduce hepatic lipids in MTP inhibited mice but spared increases in plasma AST/ALT. Moreover, acute induction of ER stress by tunicamycin increased plasma AST/ALT by 2.5-fold. This research leads to a conclusion that increases in plasma AST/ALT after MTP inhibition might be due to hepatic free cholesterol accretion and induction of ER stress.

In an effort to maximize the affect of MTP while minimizing the potentially harmful side effects associated with MTP therapy, the present invention provide % a pharmaceutical combination and method for treating hyperlipidemias using the combination. The combination comprises at least one lipid lowering agent and at least one Microsomal Triglyceride Transfer Protein (MTP) inhibitor.

It has been surprisingly found that administering this combination in mice avoids increases in plasma AST/ALT, hepatic triglyceride/free cholesterol, and ER stress. The same was evaluated in primates using Western-diet fed bonnet macaques that were fed MTP antagonists with or without lovastatin or pioglitazone. MTP antagonists decreased plasma lipids but increased AST/ALT. Animals that also received pioglitazone did not show elevated plasma AST/ALT. Accordingly, the composition and method of the present invention provides a way to treat hyperlipidemias without evidence of hepatic disease by using MTP antagonists along with agents that avoid accumulation of cellular lipids.

Example of MTP inhibitors which may be used in the compositions and methods of the present invention, include but are not limited to Ire1β, CP-346086, JTT-130, BMS-201038, AEGR-733 (Lomitapide), SLx-4090 and benzothiazole derivatives such as triamide derivatives bearing a benzothiazole core as described by Vu C B et al., in Bioorg Med Chem Lett 2009 Mar. 1; 19(5):1416-20, Epub 2009 Jan. 19, which is incorporated by reference herein as if fully set forth.

Examples of lipid lowering agents include but are not limited to statins such as e.g., atorvastatin, resovastatin, fluvastatin, pravastatin. lovastatin and simvastatin. Examples of PPARα/PPARγ agonists include but are not limited to Glitazars such as Muraglitazar, Tesaglitazar, Aleglitazar and the compound (RS)-5-(4-[2-(5-ethylpyridin-2-yl)ethoxy]benzyl)thiazolidine-2,4-dione (pioglitazone).

As used herein, the term "combination" means that the components, i.e., the MTP inhibitor and lipid lowering agent, may be administered together as a pharmaceutical composition or as part of the same, unitary dosage form. A combination also includes administering the MTP inhibitor and lipid lowering agent each separately, but as part of the same therapeutic regimen. The components, if administered separately, need not necessarily be administered at essentially the same time, although they can if so desired. Thus, the MTP inhibitor and lipid lowering agent may be administered as separate dosages or dosage forms, but at the same time. As used herein, a combination also includes separate administration at different times and in any order.

Daily dosages for the MTP inhibitor and lipid lowering agent will, of course, vary depending on a variety of factors, for example, the particular compound chosen. In general, however, satisfactory results are achieved on administration of both MTP inhibitor and lipid lowering agent in the order of 1-100 mg per day, with a preferred dosage of 50-100 mg per day. Thus for example, an $PPAR_\alpha/PPAR_\gamma$ agonist may be administered at a dosage of 1-100 mg per day and a statin may be administered at a dosage of 1-100 mg per day, as a single dose or in divided doses. The MTP inhibitor and lipid lowering agent may be administered by any conventional route, in particular enterally, e.g., orally, e.g., in the form of tablets, capsules, drink solutions, or parenterally, e.g., in the form of injectable solutions or suspensions.

MTP, a Target to Treat Hyperlipidemias:

Hyperlipidemias are major risk factors for atherosclerosis. There are two metabolic abnormalities that could lead to hyperlipidemias, over production or decreased catabolism. Significant progress has been made with statins in lowering plasma lipids by increasing their catabolism. However, attempts to control lipoprotein production have not yet been successful. ApoB and MTP are prime candidates to curb lipoprotein production. Since apoB does not have a biochemical activity amenable to through put screening, siRNA technology has been used to lower its production.

In contrast to apoB, due to its lipid transfer activity, MTP has been a favorite target to identify small molecule inhibitors and to lower plasma lipids. Indeed several MTP antagonists have been identified that decrease lipoprotein production and plasma lipids. Unfortunately, these drugs exhibit two types of tissue specific side effects. The first side effect is related to the inhibition of chylomicron assembly by enterocytes and manifests as gastrointestinal disturbances such as steatorrhea and diarrhea. These disturbances have been successfully avoided by administering MTP inhibitors 4 h after the supper.

Recently, Ire1β has been shown to down regulate intestinal MTP indicating that its up-regulation might be a viable target for lowering intestinal MTP. The second side effect is related to the inhibition of hepatic lipoprotein assembly and secretion. In about 10-30% of the individuals, MTP inhibitors increase plasma levels of liver enzymes, mainly AST and ALT. Thus, there is a critical need for novel approaches to inhibit MTP without causing steatosis. It is proposed that intestine-specific inhibition of MTP might be beneficial because of the inherent property of the intestine to self-renew. In fact, intestine-specific MTP inhibitor, JTT-130, has been shown to lower plasma triglyceride and LDL cholesterol in guinea pigs without increasing hepatic triglyceride. Similarly, another intestine-specific compound, SLx-4090, has been shown to lower plasma lipids. Thus, an intestine-specific inhibition of MTP might avoid hepatic toxicity. Here, we propose an alternate possibility.

As MTP primarily transfers neutral lipids in vitro and helps in the transport of neutral lipids in vivo by assembling apoB-lipoproteins, it has been assumed that toxicities associated with MTP inhibition and genetic ablation are due to the accumulation of neutral lipids. We should, however, realize that synthesis and storage of neutral lipids (triglycerides and cholesterol esters) is beneficial in avoiding toxicities associated with excess free fatty acids and free cholesterol. The question then arises why MTP inhibition increases plasma hepatic enzymes. A common explanation provided is that MTP inhibition leads to higher, possibly toxic, amounts of neutral lipids in the liver. However, there are reports indicating that, at least, short-term use of MTP inhibitors does not always lead to an overt accumulation of hepatic lipids. We are not aware of studies describing a clear-cut relationship between the accumulation of fat in the liver and the appearance of hepatic enzymes in the plasma. Assuming that the toxicity due to MTP antagonists is associated with hepatic fat accumulation, it can conceivably be avoided by upregulating mitochondrial and peroxisomal oxidation of fatty acids. PPARs are nuclear hormone receptors that enhance fatty acid oxidation by peroxisomes. Potent PPARα agonists decrease hypercholesterolemia and atherosclerosis in Idlr$^{-/-}$ mice. A combined use of MTP inhibitors and PPARα activators has been speculated before. Still, experimental evidence for their beneficial use is lacking. Hence, there is a need to question the fundamental paradigm that MTP inhibitors increase plasma hepatic enzymes by augmenting cellular concentrations of triglycerides and to find new ways to circumvent hepatosteatosis.

Cellular triglyceride buildup is a key feature of MTP inhibition. Triglyceride synthesis involves fatty acid uptake, intracellular transport to microsomes by fatty acid binding proteins, and acylation with glycerol by several monoacylglycerol and diacylglycerol acyltransferases. Inhibition of these steps will likely reduce cellular triglyceride levels. In this respect, repression of liver fatty acid binding protein along with MTP inhibition has been shown to lessen steatosis. Several studies have shown that flavonoids inhibit triglyceride transfer activity of MTP. These compounds affect several other biological pathways and have pleiotropic effects. For example, Taxifolin, a plant flavonoid, inhibits triglyceride synthesis and MTP activity without increasing cellular lipids. Therefore, combined inhibition of triglyceride synthesis and MTP activity might avoid triglyceride accumulation. This is supported by observations that DGAT1 deficient mice do not develop hepatic steatosis, demonstrate increased energy expenditure and have significantly lower levels of triglycerides in lipogenic tissues. Thus, DGAT inhibition with MTP antagonism offers an attractive opportunity for therapeutic interventions in obese and diabetic patients. Here, we are hypothesizing that the liver injury might be due to high free cellular cholesterol levels and are proposing new approaches to avoid toxicities associated with MTP inhibition.

The ER Stress Response:

In vertebrates, three major integral membrane proteins [Inositol requiring enzyme 1 (IRE1), protein kinase-like ER kinase (PERK), and activating transcription factor 6 (ATF6)] monitor the ER stress. These three proteins act in parallel to transmit information across the ER membrane to decrease protein synthesis and induce expression of transcription factors to enhance the synthesis of chaperones. IRE1 and PERK have similar lumenal stress-sensing domains, which normally bind to an ER chaperone Bip. When the amounts of misfolded proteins increase, Bip dissociates from IRE1 and PERK. This in turn results in the oligomerization and activation of these kinases. Activation of IRE1 unmasks an endoribonuclease activity. This activity mediates a unique splicing event generating a distinct shorter, functional form of XBP1. XBP1 is a transcription factor and activates several stress responsive genes. Activated PERK phosphorylates a subunit of eukaryotic translation initiation factor 2 (eIF2α) in the cytosol and inhibits general protein synthesis, thereby inhibiting further synthesis of toxic misfolded proteins. Phosphorylated eIF2α also mediates a specific and selective enhancement of ATF4 translation. This transcription factor up-regulates a number of UPR-regulated genes, such as C/EBP-homologous protein (CHOP) and Bip. In contrast to the IRE1 and PERK activation, ER stress facilitates the egress of ATF6 from the ER to the Golgi. In the Golgi, ATF6 is cleaved sequentially by the site-1 and site-2 proteases releasing an active ATF6, which also up-regulates a group of genes encoding ER resident molecular chaperones and folding enzymes.

It has been shown that ER stress is induced in macrophages with high levels of intracellular free cholesterol. In the case of cholesterol-loaded macrophages, upstream ER stress signaling molecules are required for early macrophage viability, although a distal branch involving the ER stress response effector CHOP triggers apoptosis. In view of these findings, the Applicants of the present invention explored whether free cholesterol accumulation after gene deletion induces ER stress in other tissues.

Plasma AST/ALT, Markers of Hepatic Injury:

Aspartate aminotransferase (AST) and alanine aminotransferase (ALT) are hepatic enzymes involved in intermediary metabolism. AST and ALT catalyze reversible reactions that transfer an amino group from the amino acids aspartate and alanine to the tri-carboxylic acid (TCA) cycle intermediate α-ketoglutarate to form oxaloacetate and pyruvate, respectively. These enzymes allow for the regeneration of TCA cycle and glycolytic intermediates in times of low glucose availability. Two isoforms are present in humans for each enzyme; AST-1, AST-2, ALT-1, ALT-2. AST-1 is a cytosolic enzyme that localizes to the heart and red blood cells, but it is also found in the liver. AST-2 is a mitochondrial enzyme that is only found in the liver. It is assumed that this form of AST is the major form found in serum. ALT-1 is a cytosolic enzyme that is present in the liver, kidney and skeletal muscle. It is thought that this form of ALT is the major form found in serum. ALT-2 mRNA have been found in muscle, adipose tissue and liver; conflicting data exists as to whether the ALT-2 protein is found in hepatocytes.

The measurements of serum AST and ALT are part of a normal liver function panel and are the most commonly used test to ascertain liver function. They are considered to be sensitive markers for parenchymal damage and/or inflammation. It is currently held that serum aminotransferase elevations are a result of the release of intracytosolic contents from dying hepatocytes, but many recent publications have shown significant elevations in serum ALT with little to no indication of parenchymal inflammation/injury. Several recent reports have also shown that serum AST/ALT values are predictive of the progression of non-alcoholic fatty liver disease and the metabolic syndrome, however, mechanisms for their release in these disorders are unknown.

The present invention provides compositions and methods of treatments that alters mechanisms that lead to augmented release of AST/ALT into the plasma of animals exposed to MTP inhibitors. This leads to the avoidance of toxicities associated with MTP inhibition by lowering hepatic free cholesterol would indicate that MTP inhibitors could be used to treat different forms of hyperlipidemias, such as familial combined hyperlipidemia, familial hypercholesterolemia. Using the compositions and methods of the present invention makes MTP targeting a viable approach to lowering plasma lipids.

That is, data obtained and discussed herein highlights a significant relationship between MTP inhibition and aberrant elevations in plasma transaminases. These studies demonstrate that MTP inhibition leads to enhanced cellular free cholesterol and that toxicities associated with MTP inhibition can be avoided by reducing hepatic free cholesterol. Furthermore, the present invention indicates that MTP inhibitors could be used in combination with cholesterol lowering agents to treat hyperlipidemias.

Avoiding toxicities associated with MTP inhibition by lowering cellular free cholesterol levels challenges the current paradigm that toxicities observed in hepatosteatosis are mainly due to the accumulation of neutral lipids and provide a new paradigm, that other lipids, besides triglycerides, must be taken into account when treating and explaining toxicities associated with hepatic lipid accumulation.

MTP antagonists are currently used only for limited purposes, such as, lowering lipids in familial hypercholesterolemia and controlling obesity in dogs. However, in view of the present invention, the side effects associated with MTP inhibition can be avoided by lowering free hepatic cholesterol. Accordingly, the combination of the present invention includes not only MTP but at least one lipid lowering agent, both in an amount effective to treat hyperlipidemias.

As discussed further below and in the examples, the lipid lowering agents including statins, successfully lower plasma lipid levels and decrease in plasma cholesterol. Unexpectedly, several beneficial effects of statins have been observed that are, most likely, unrelated to reduction in plasma lipids and are usually referred to as "pleiotropic effects." The present application indicates that statins not only reduce plasma lipids but they also decrease cellular free cholesterol. Accordingly, most likely some of the pleiotropic effects of statins might be related to reductions in cellular free cholesterol. The composition of the present invention has lead to the understanding how in vivo exposure of MTP inhibitor and other effective lipid-lowering agents in attenuating dyslipidemia. The present invention provides mechanistic data that allows determining how MTP inhibitor-linked excess free cholesterol contributes to hepatic injury. MTP inhibition might be particularly useful for individuals with inherited dyslipidemia who are unable to reach an adequate LDL cholesterol goal.

The idea that hepatic toxicities associated with MTP inhibition are due to cellular free cholesterol accumulation is in itself novel. Moreover, the present invention provides a composition and method for lowering of cellular free cholesterol so as to avoid toxicities associated with MTP antagonists and to treat hyperlipidemias.

The following examples are meant to further illustrate the invention and are not intended in any way to limit the scope of the invention.

Example I

Figure 1:
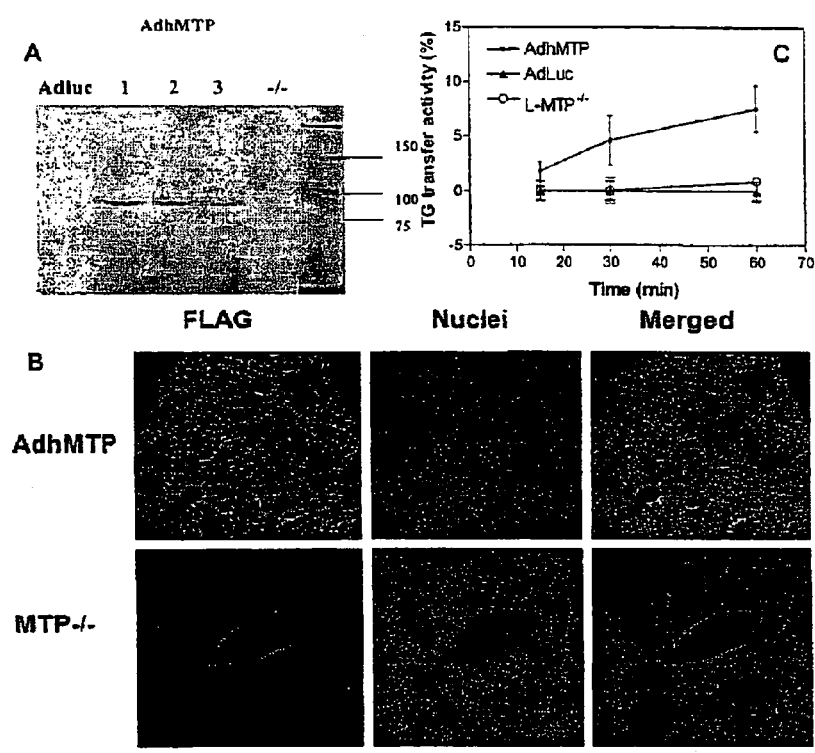
FIG. 1. Livers from L-MTP−/− mice were analysed for the expression of hMTP-FLAG by Western blot analysis (A) and immunohistochemistry (B). Livers were also used to determine triglyceride transfer activity (C).

Changes in Hepatic Lipids and Plasma AST/ALT are Due to Specific Ablation of mttp Gene To find out if mttp gene ablation enhances plasma AST/ALT levels, we used mice that were only deficient in hepatic MTP. MTP$^{fl/fl}$ (WT) mice were crossed with Alb-Cre mice to obtain liver-specific MTP deletion (L-MTP$^{-/-}$). These L-MTP$^{-/-}$ mice were injected with adenoviruses expressing luciferase (Ad-Luc) or human MTP (Ad-hMTP-FLAG) to re-express MTP. Western blotting (FIG. 1A), immunohistochemistry (FIG. 1B), and activity measurements (FIG. 1C) showed that L-MTP$^{-/-}$ mice lack MTP expression. By contrast, livers from mice injected with Ad-hMTP-FLAG had an immunoreactive band of ~97 kDa, exhibited intense cytoplasmic staining and showed robust triglyceride transfer activity (FIG. 1). These studies show that livers of L-MTP$^{-/-}$ mice lack triglyceride transfer activity and injection of Ad-hMTP-FLAG results in the expression of triglyceride transfer activity.

Figure 2:
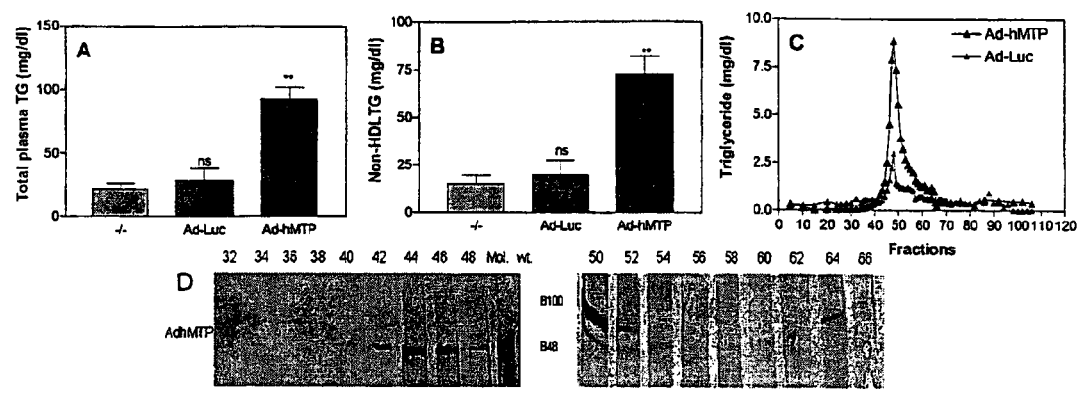
FIG. 2. A, B: changes in T levels of plasma and apoB-lipoproteins after the transduction of different viruses. C: FLPC analysis showing plasma triglyceride distribution. D: Western blot analysis of apoB in different FPLC fractions from Panel C.

Next, we measured the effect of mttp gene ablation and hMTP expression on apoB-lipoprotein assembly and secretion (FIG. 2). L-MTP$^{-/-}$ mice were divided into 3 groups of 3 animals each. Groups 1 and 2 received tail vein injections of Ad-hMTP and Ad-Luc, respectively. Group 3 received PBS injections. After 48 h, mice were fasted for 3 h to reduce intestinal absorption, and injected with poloxamer 407 (P407, 30 mg/mice) to inhibit plasma lipoprotein lipase and clearance of apoB-lipoproteins. After 3 h of p407 injection, plasma and tissues were collected. Plasma triglyceride increased in Ad-hMTP (3-fold) compared to control and luciferase groups (FIG. 2A), mostly due to increases in non-HDL apoB-lipoproteins (FIG. 2B). No significant differences were observed in HDL triglyceride and total cholesterol in these groups (not shown). Plasma FPLC analysis revealed that mice expressing Ad-hMTP had higher triglyceride in VLDL/LDL fractions than in Ad-Luc injected mice (FIG. 2C). Western blot analyses of FPLC fractions showed that apoB was distributed in several fractions (FIG. 2D). We interpret these data to suggest that expression of hMTP helps in the assembly and secretion of apoB-lipoproteins.

We also studied the effect of hepatic mttp gene deletion and expression of human MTP on plasma lipids and hepatic enzymes (FIG. 3). Hepatic mttp gene deletion significantly reduced total, non-HDL apoB-lipoproteins, and HDL triglyceride (FIGS. 3A-C). Injection of Ad-Luc had no significant effect on plasma triglycerides, but injection of Ad-hMTP significantly increased triglyceride in total plasma and apoB-lipoproteins (FIGS. 3A-C). Ablation of hepatic MTP or its re-expression had very little effect on plasma cholesterol (FIGS. 3D-F). These data indicate that MTP is a predominant determinant of plasma triglyceride but not of plasma cholesterol.

The changes in hepatic lipids in these mice were then studied and the results are provided below. Deletion of mttp significantly enhanced hepatic triglyceride (FIG. 3G), as well as total and free cholesterol (FIGS. 3H-I), but had no effect on hepatic cholesteryl esters (FIG. 3J). Expression of Ad-Luc had no significant effect on hepatic lipids. By contrast, expression of human MTP significantly lowered hepatic triglyceride (FIG. 3G) and free cholesterol (FIG. 3I). Now, hepatic free cholesterol levels were not significantly different from WT mice (FIG. 3I).

Analysis of plasma AST/ALT indicated that the absence of hepatic MTP increases plasma ALT/AST levels compared to MTP$^{fl/fl}$ (WT) and expression of human MTP, but not luciferase, reduces these levels (FIGS. 3K-L). These studies indicate that mttp gene deletion increases hepatic triglyceride and free cholesterol as well as plasma AST/ALT. These increases can be avoided by expressing MTP. Therefore, there is a significant cause and effect relationship between MTP ablation, increases in hepatic triglyceride/free cholesterol, and increases in plasma AST/ALT.

Example II

Figure 4A:
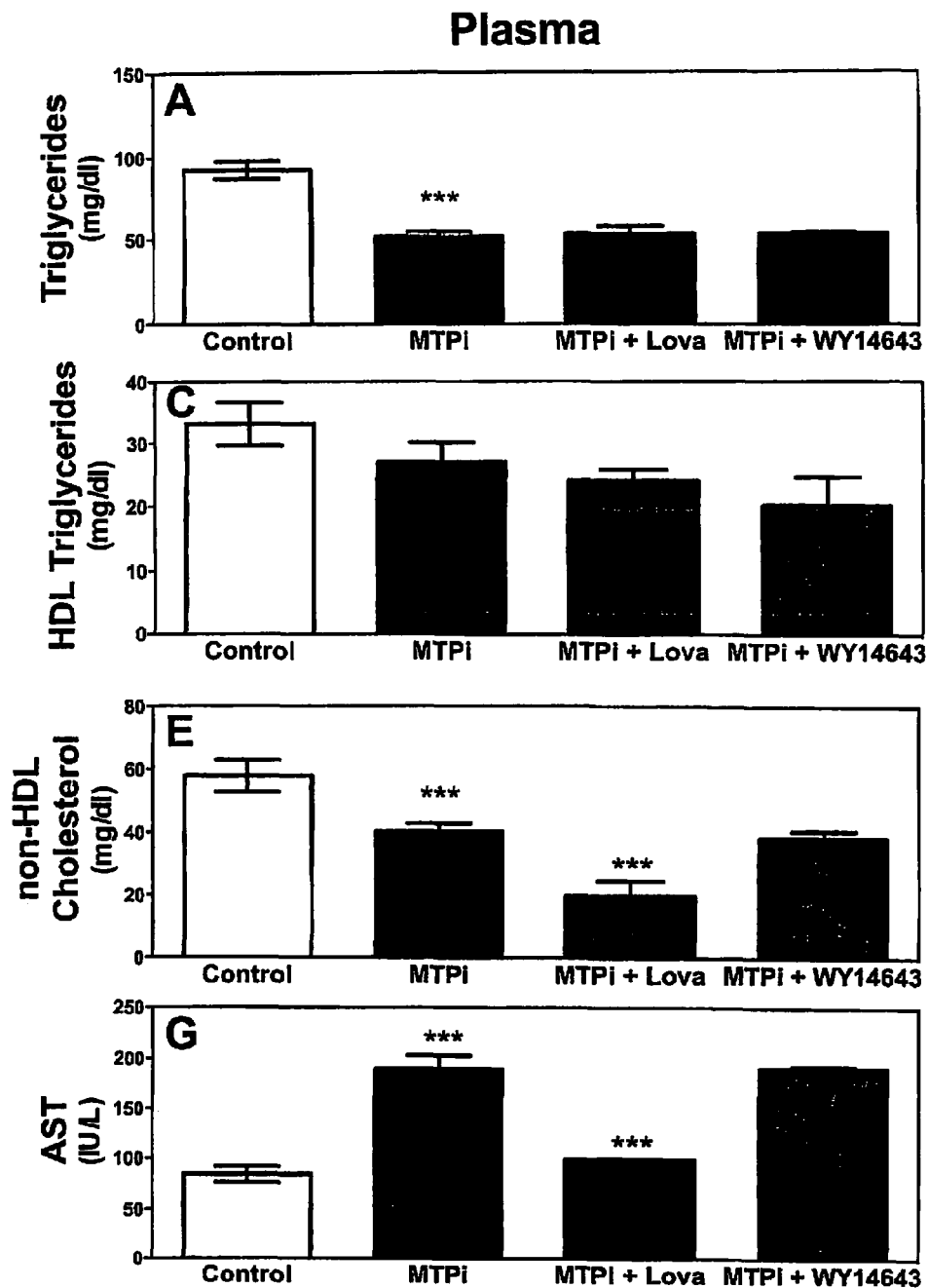
FIGS. 4a and 4b. Effect of MTP inhibitor (CP-34086) on plasma lipids and lipoproteins in C57Bl/6J mice fed western diet ad libitum for 8 weeks. MTP inhibitor solubilzed in DMSO was administered orally for one week (15 mg/kg/day) along with either DMSO (MTPi), lovastatin (50 mg/kg/day), or WY14643 (10 mg/kg/day). Control mice were gavaged with DMSO only. Stars on MTPi+Lovastatin and MTPiwy14643 represent individual comparisons with MTPi groups. *, p, 0.05, P, 0.01, *, $p<0.001$.
Figure 4B:
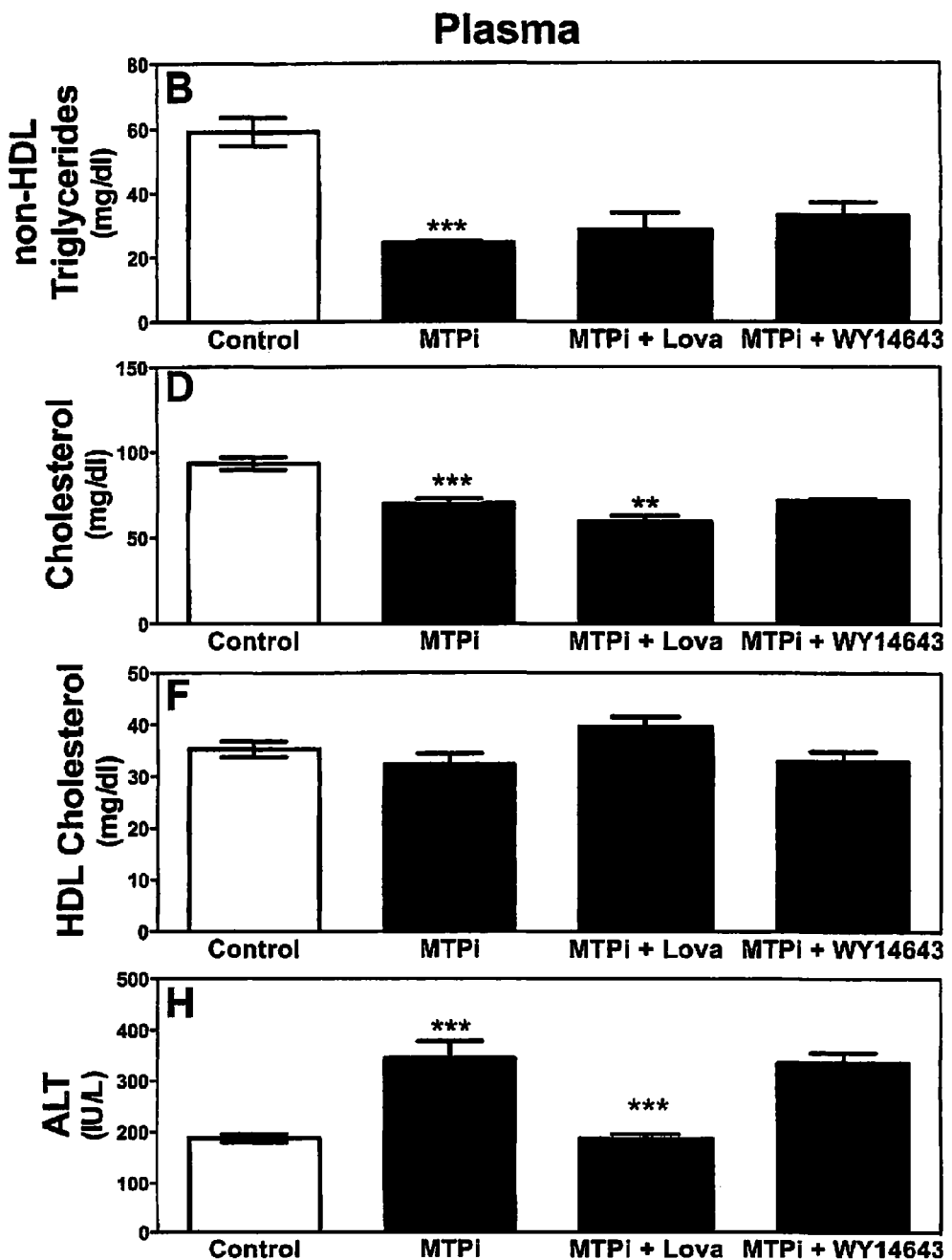

Increases in Plasma AST/ALT Due to Chemical Inhibition of MTP are Avoided by Free Cholesterol Lowering Drugs The effect of MTP inhibitors in C57Bl/6J mice fed western diet for 8 weeks was studied and the results are shown in FIG. 4. Control group (n=4) received daily oral gavage of DMSO alone. MTPi group received 15 mg/kg/day MTP inhibitor CP-346086 (MTPi) once daily. MTPi+lovastatin or MTPi+WY14643 groups got either lovastatin or WY14643 along with MTP inhibitors daily. After 1 week, mice fed with MTPi had significantly lower total and LDL triglyceride, and LDL cholesterol (FIG. 4). Plasma total and HDL cholesterol were unaffected by MTPi. Combined treatment of MTPi and lovastatin decreased plasma LDL cholesterol. On the other hand, WY14643 did not affect plasma lipids. Next, we measured changes in plasma hepatic enzymes (FIGS. 4G-H). MTPi treatment significantly enhanced plasma AST/ALT. WY 14643 had no significant effect on these increases. By contrast, animals treated with MTPi and lovastatin had significantly lower levels of AST/ALT compared to MTPi group and their levels were similar to those in control animals. These studies indicate that apart from lowering plasma triglyceride, MTPi enhances plasma AST/ALT and these increases can be avoided by the co-administration of lovastatin.

Figure 5A:
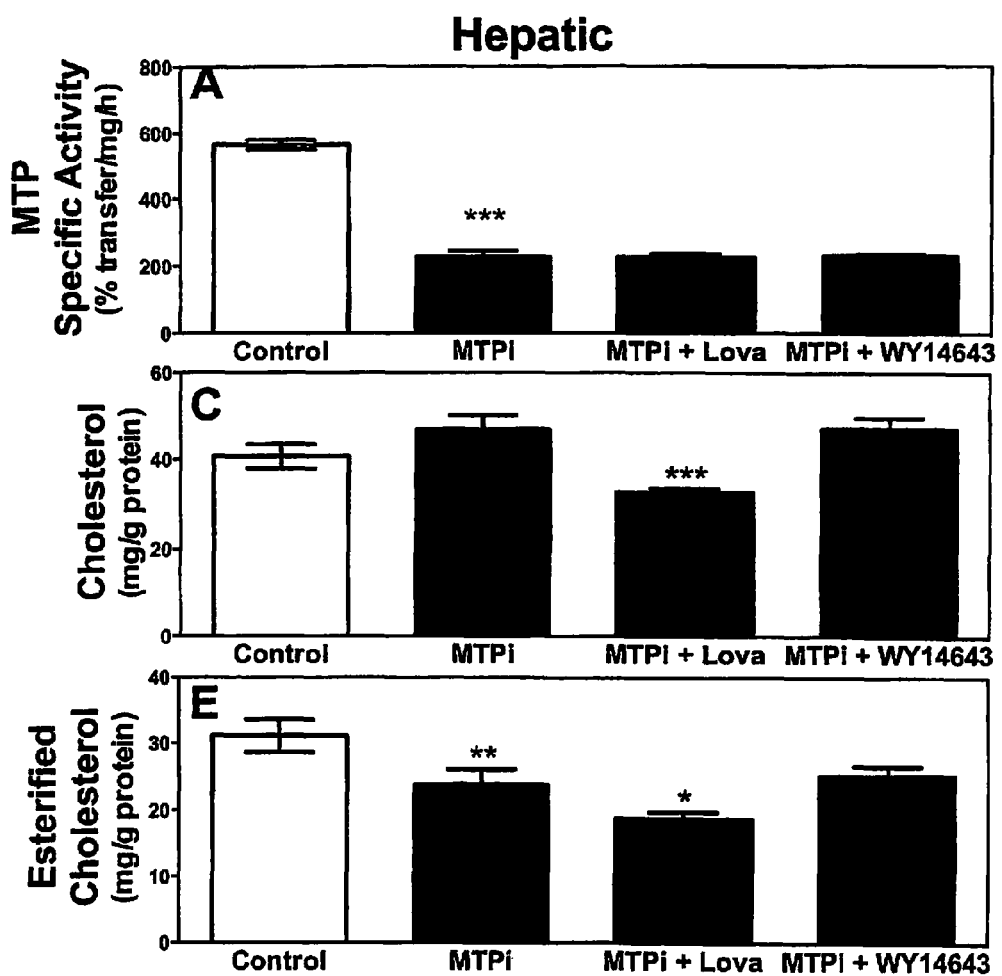
FIGS. 5a and 5b. Liver samples from FIG. 4 were used to measure MTP activity (A) and hepatic lipids (B-E). Stars on MPTi group represent comparison between Control and MTPi groups. Stars on MTPi+Lovastatin and MTPi+WY14643 represent individual comparisons with MPTi groups. *, $p<0.05$; , $p<0.01$; *$p<0.001$.
Figure 5B:
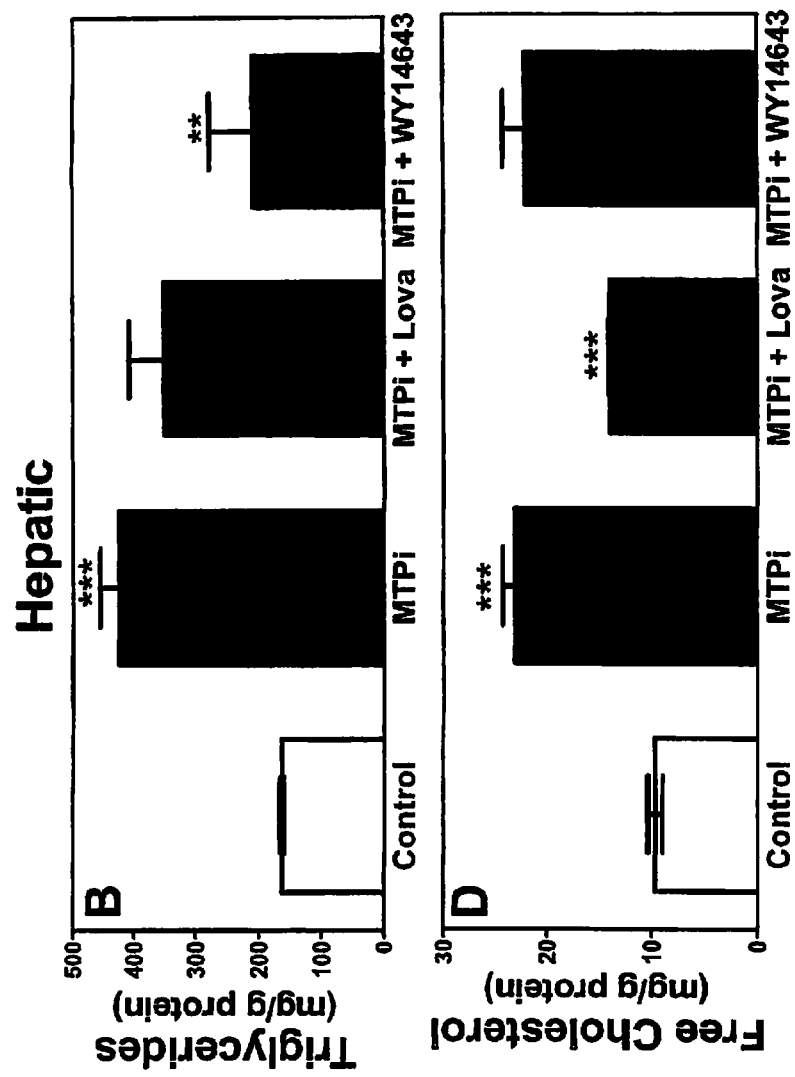

The effect of MTP inhibition and co-administration of other drugs on MTP activity is shown in FIG. 5A. As expected, MTP activity was significantly inhibited in MTPi treated groups and lovastatin or WY14643 had no further effect on this activity. MTPi significantly enhanced hepatic triglyceride and these increases were avoided in MPi+WY group but not in lovastatin group (FIG. 5B). MTPi increased hepatic free cholesterol and decreased cholesterol esters (FIGS. 5D-E). Compared to MTPi group, lovastatin treated animals had significantly lower total, free and esterified cholesterol (FIGS. 5C-E). WY had no significant effect on hepatic cholesterol levels. Thus, lovastatin abrogates increases in hepatic free cholesterol after MTPi exposure, whereas WY avoids increases in hepatic triglyceride.

Figure 6A:
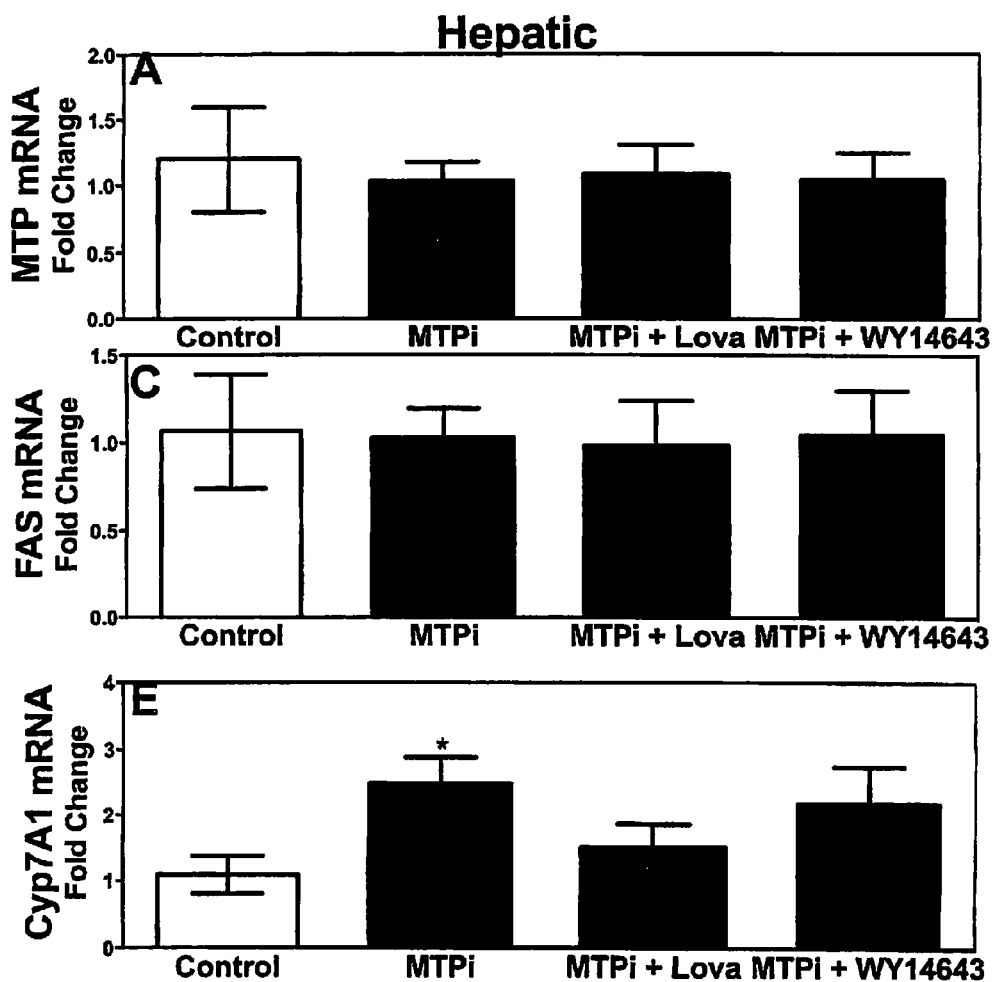
FIGS. 6a and 6b. Liver samples from FIG. 16 were used to isolate total mRNA and to quantify expression of different candidate genes. Statistical analyses were as described in FIGS. 16-17.
Figure 6B:
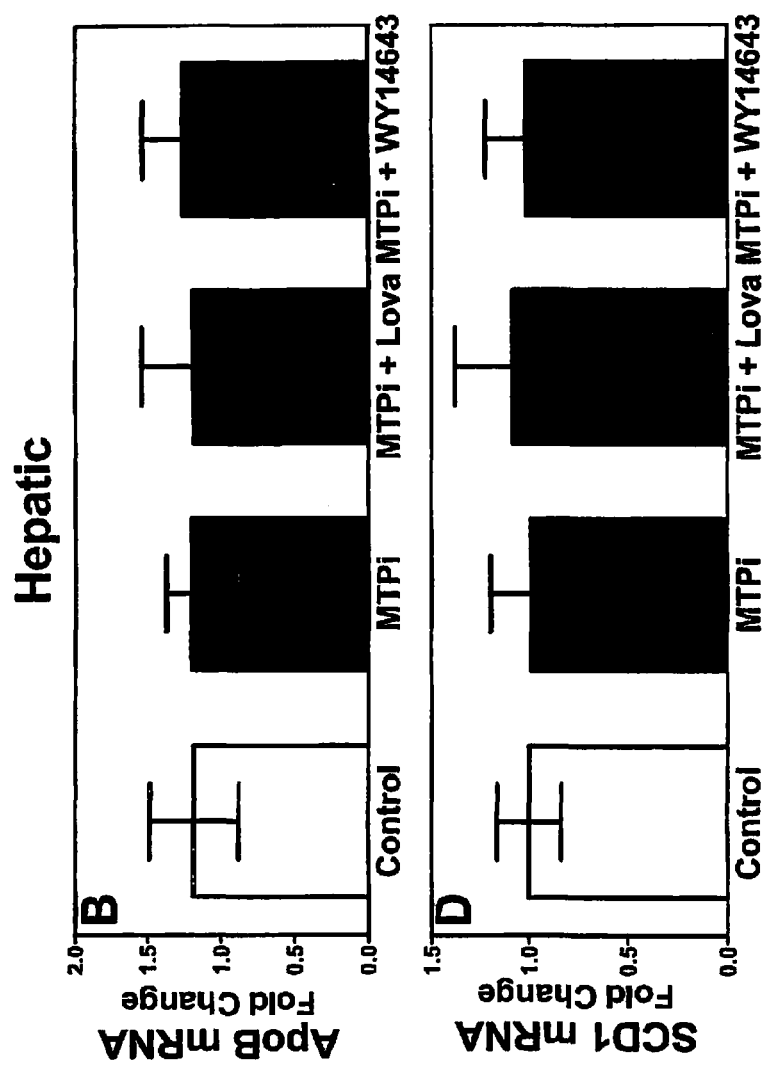

Changes in the expression of different genes involved in lipid metabolism and the results are shown in FIG. 6. Feeding of MTP inhibitor and other compounds had no effect on the mRNA levels of MTP (FIG. 6A) and apoB (FIG. 6B) indicating no effect on the expression of genes involved in lipoprotein assembly. We also measured changes in mRNA expression of genes involved in fatty acid synthesis. Both FAS (FIG. 6C) and SCD-1 (FIG. 6D) mRNA did not change. We also measured changes in bile acid metabolism. CYP7A1, a rate-limiting enzyme in bile acid biosynthesis that is regulated by cellular cholesterol, was increased in MTPi treated animals. Its levels decreased in MTPi+Lovastatin group but remained similar in MTPi+WY group to those seen in MTPi group. These studies indicate that MTPi do not affect genes involved in fatty acid and lipoprotein synthesis. But, genes that are responsive to cellular cholesterol are changed when exposed to MTPi and these changes are avoided when animals received lovastatin.

Example III

Reduction of Hepatic Free Cholesterol and Triglyceride Using Pioglitazone

In the above studies lovastatin reduced free cholesterol but had no effect on hepatic triglyceride. By contrast, WY14643 decreased hepatic triglyceride and had no effect on free cholesterol. These studies showed that increases in AST/ALT could be avoided by lowering hepatic free cholesterol but not by triglyceride. Nevertheless, accumulation of hepatic triglyceride will not be tolerated over a long term. Therefore, we considered the possibility of combining lovastatin and WY14643 with MTPi. However, combination of three drugs is not going to be a favorable therapeutic approach. Therefore, we sought to find another agent that could reduce both free cholesterol and triglyceride in the liver and that could be used in combination with MTPi. In preliminary studies, we found that omega 3 fatty acids that act as agonists of PPARα/PPARγ reduced both hepatic free cholesterol and triglyceride. Therefore, we evaluated pioglitazone, which is known to activate both PPARα and PPARγ, for its efficacy in decreasing hepatic lipids and its possible use in combination with MTPi.

Figure 7A:
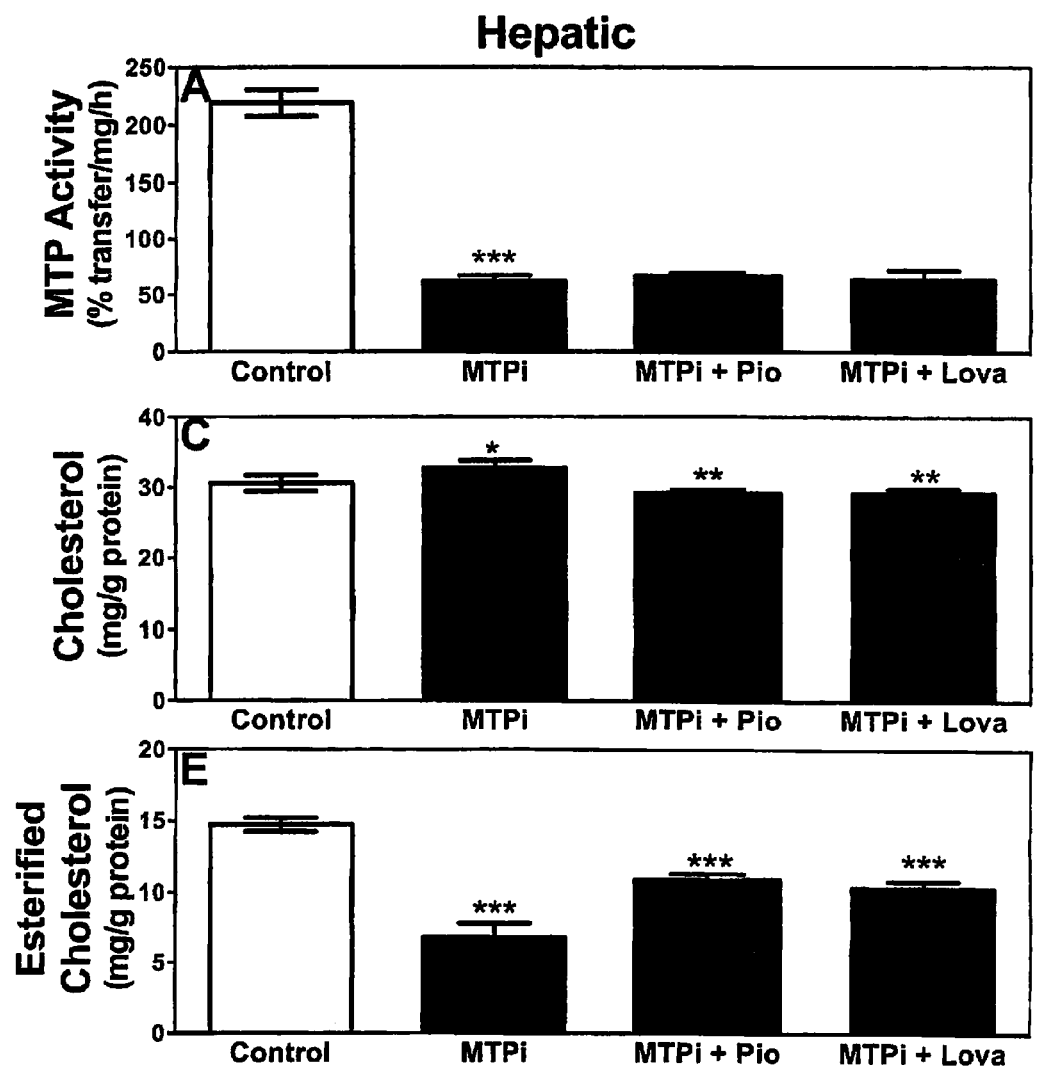
FIGS. 7a and 7b. Mice were fed western diet for five weeks. In the last week, they either received DMSO (control, n+3), MTPi, MTPi+pioglitazone, or MTPi+lovastatin. Livers were collected and used to measure MTP activity (A), triglyceride (B), total cholesterol (C), free cholesterol (D), esterified cholesterol (E) and free fatty acids (F).
Figure 7B:
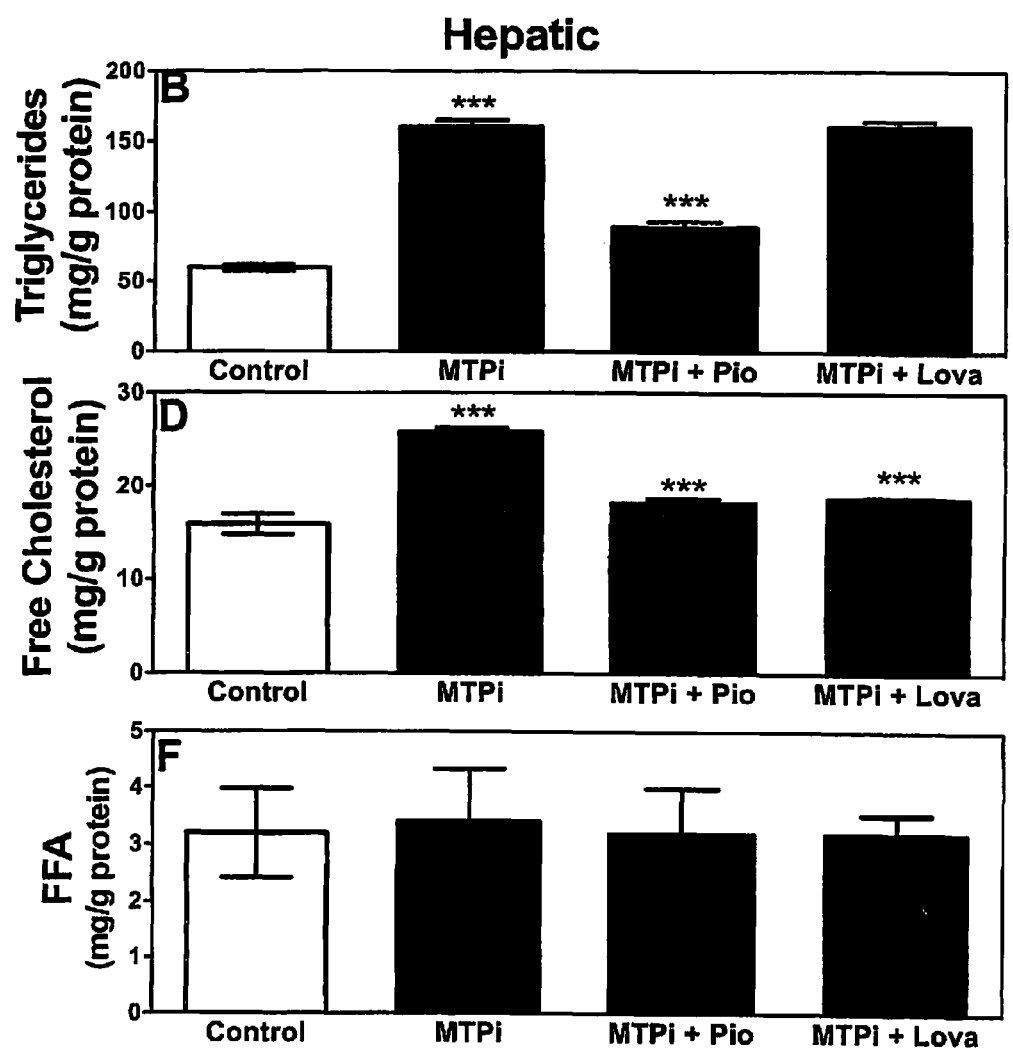

As expected, MTPi significantly reduced MTP activity (FIG. 7A). This reduction was unaffected by pioglitazone or lovastatin. MTP inhibition significantly increased hepatic triglycerides (FIG. 7B). This increase was not affected by lovastatin treatment. However, pioglitazone treatment avoided increases in liver triglycerides. Hepatic free cholesterol was increased in MTPi treated animals and these increases were not seen in lovastatin and pioglitazone treated animals (FIG. 7D). MTP inhibition significantly reduced cellular cholesteryl esters; their levels were increased in lovastatin and pioglitazone treated group. All these treatments had no significant effect on hepatic free fatty acids levels. These studies indicate that increases in free cholesterol after MTP inhibition can be avoided by lovastatin and pioglitazone. Pioglitazone, in addition, reduces hepatic triglycerides. Therefore, MTPi and pioglitazone may be beneficial therapeutic combination.

Figure 8A:
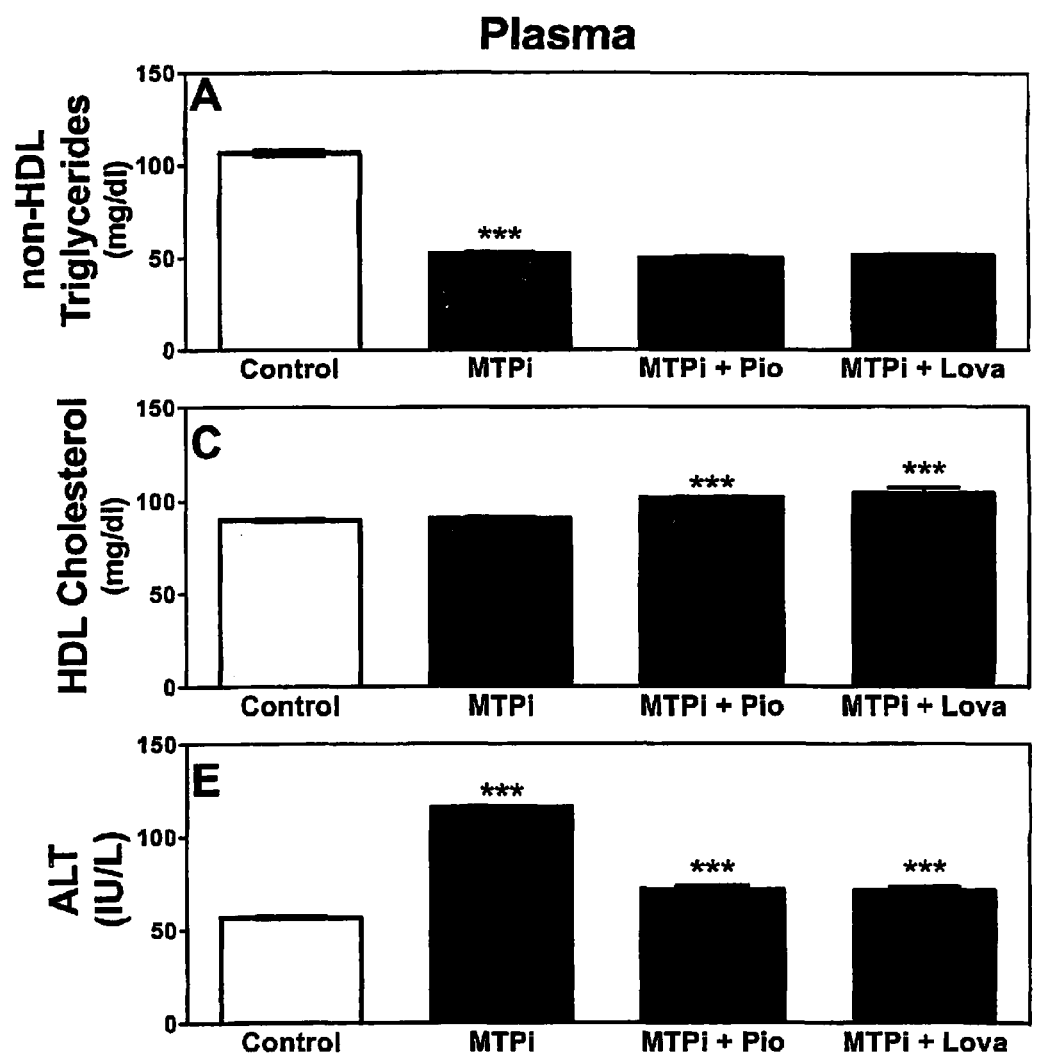
FIGS. 8a and 8b. Plasma was obtained from animals described in FIG. 7 and used to measure triglyceride (A) and cholesterol (B) in apoB-lipoproteins. In addition, HDL cholesterol (C), plasma free fatty acids (D), ALT (E), and AST (F) levels were measured.
Figure 8B:
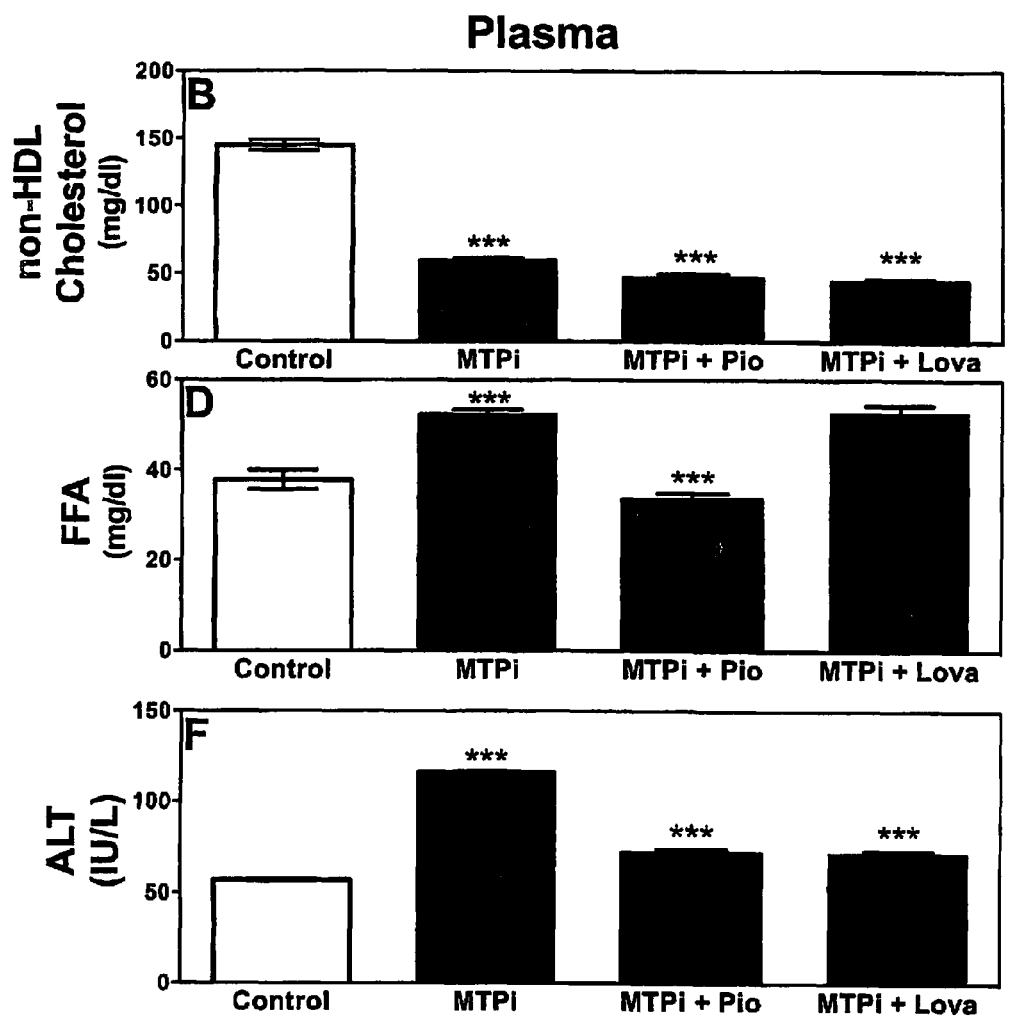
Figure 9A:
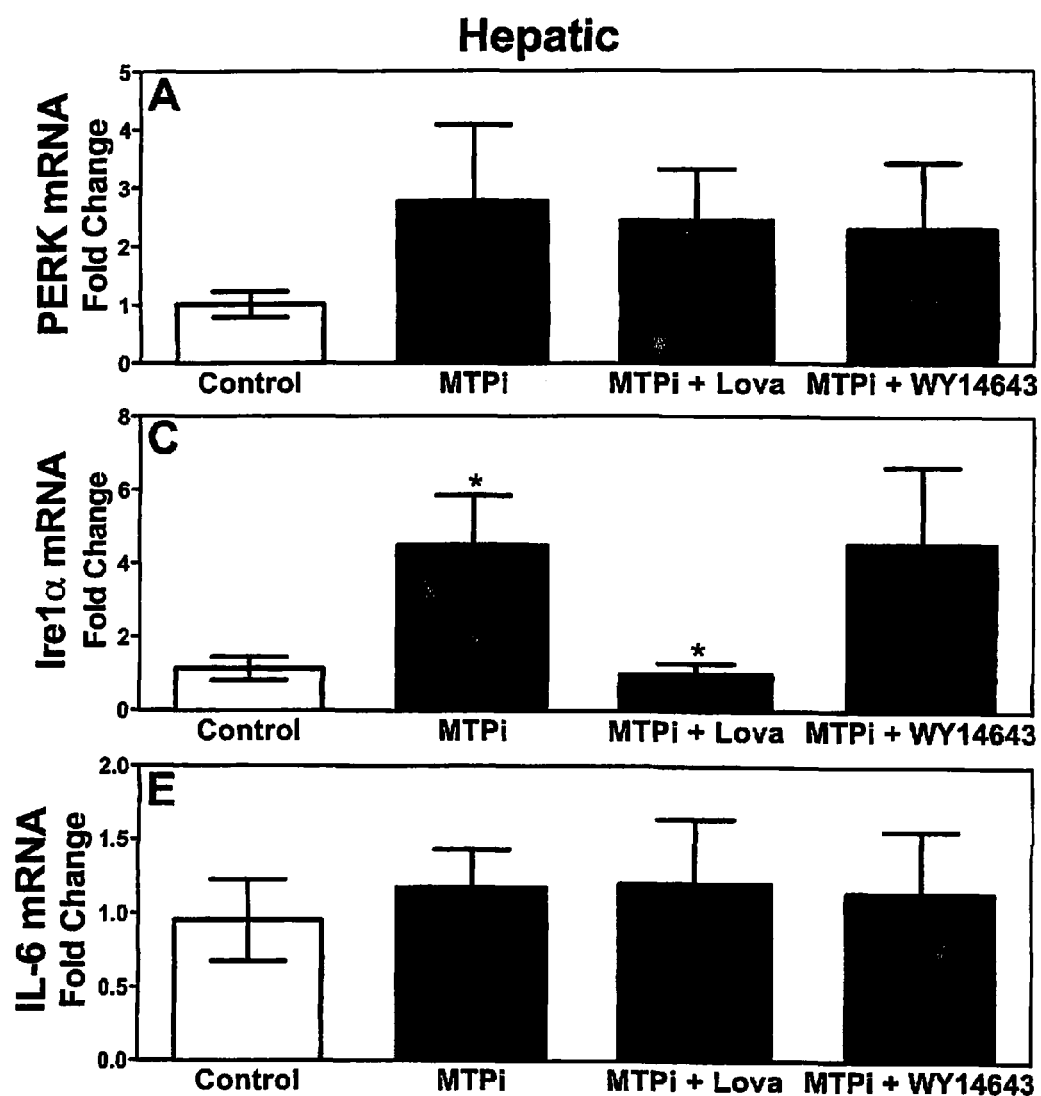
FIGS. 9a and 9b. C57B/6J mice were fed a western diet for 8 weeks and then treated with MTP inhibitor and other indicated compounds for 8 days as described in FIG. 16. Liver samples were used to isolate mRNA and to quantify mRNA levels with different candidate genes. Stars on MTPi group represent comparison with the control group. Stars on MTPi+lovastatin and MTPi+WY14643 represent their individual comparisons with MTPi group. *, $p<1.05$; $p<0.01$; *$p<001$.
Figure 9B:
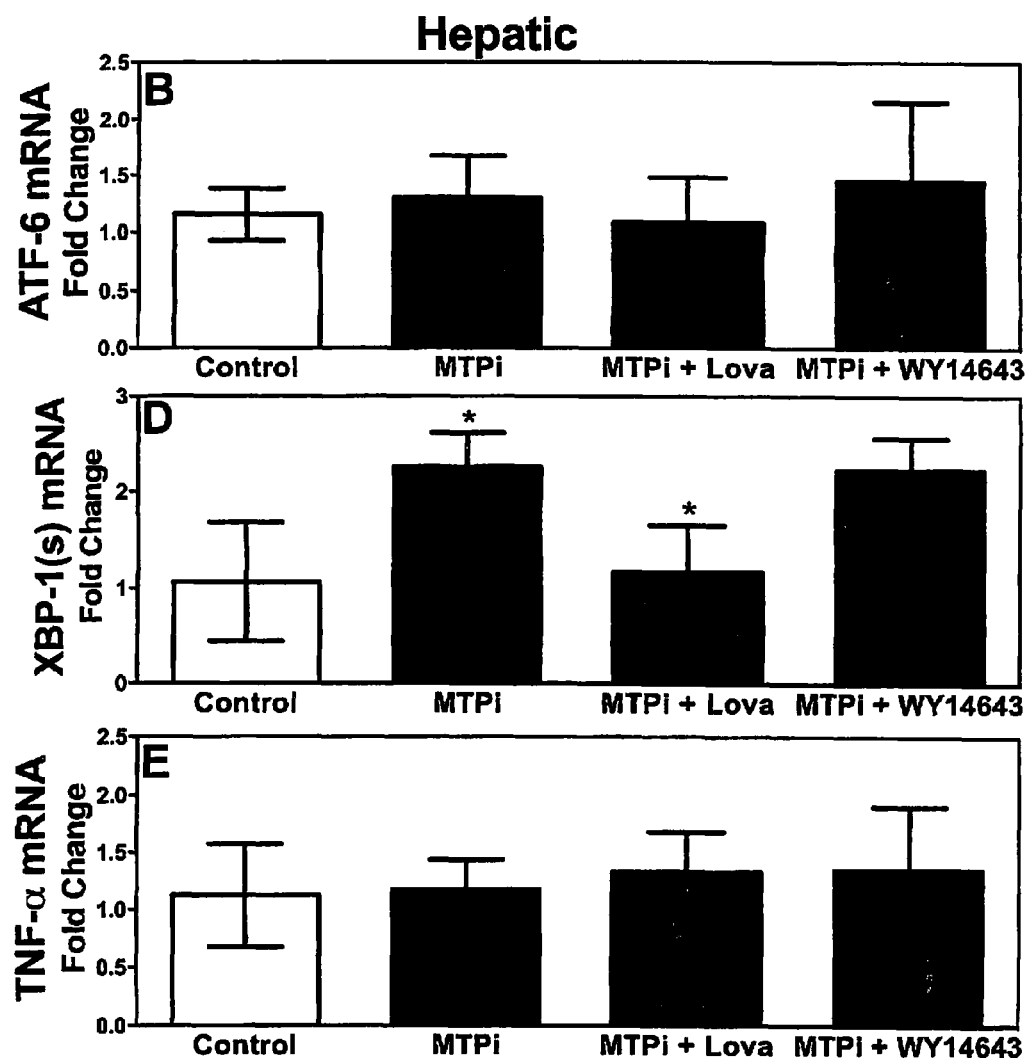

Changes in plasma lipids and AST/ALT levels were studied and the results are shown in FIG. 8. MTPi significantly reduced triglyceride (FIG. 8A) and cholesterol in apoB-lipoproteins. MTPi did not affect but lovastatin and pioglitazone slightly increased plasma HDL cholesterol (FIG. 8C). MTPi enhanced plasma free fatty acids and these levels were not affected by lovastatin. However, pioglitazone treated animals had free fatty acids that were similar to those seen in high fat fed controls (FIG. 8D). Both AST/ALT levels were increased in MTPi treated animals. These increases were significantly lower in lovastatin and pioglitazone treated animals. These studies indicate that hepatic increases in triglyceride and free cholesterol due to inhibition can be avoided by co-administration of pioglitazone. Moreover, increases in AST/ALT after MTP inhibition are also avoided by pioglitazone. These data indicate that administration of pioglitazone along with MTPi can be a beneficial approach to lower plasma lipids and avoid cellular accumulation of triglyceride and free cholesterol, Example IV MTP Inhibition and ER Stress From the above studies the mechanisms that lead to release of cellular AST/ALT after MTP inhibition was beginning to be understood. To understand mechanisms that might contribute to increases in plasma aminotransferases, we measured genes involved in ER stress and inflammation. MTPi and other compounds had no significant effect on mRNA levels of PERK and ATF-6 (FIGS. 9A-B). MTPi significantly enhanced Ire1α mRNA (FIG. 9C) and spliced form of XBP-1 (FIG. 9D), a downstream target of Ire1α. These increases were abrogated in MTPi+lovastatin group, but WY14643 had no effect on these increases (FIG. 9). Next, we measured mRNA levels of genes involved in inflammatory response. Interleukin-6 and TNFα mRNA were not affected by these treatments, perhaps, indicating less involvement of inflammatory response. We are aware that these studies need to be substantiated by measuring protein levels and are in the process of doing these experiments. Nonetheless, these preliminary studies indicate that MTPi increases hepatic free cholesterol and Ire1α mRNA as well as plasma aminotransferases and these augmentations can be abrogated by the co-administering lovastatin.

Example V

ER Stress Increases Plasma AST/ALT Levels in Mice

Figure 10:
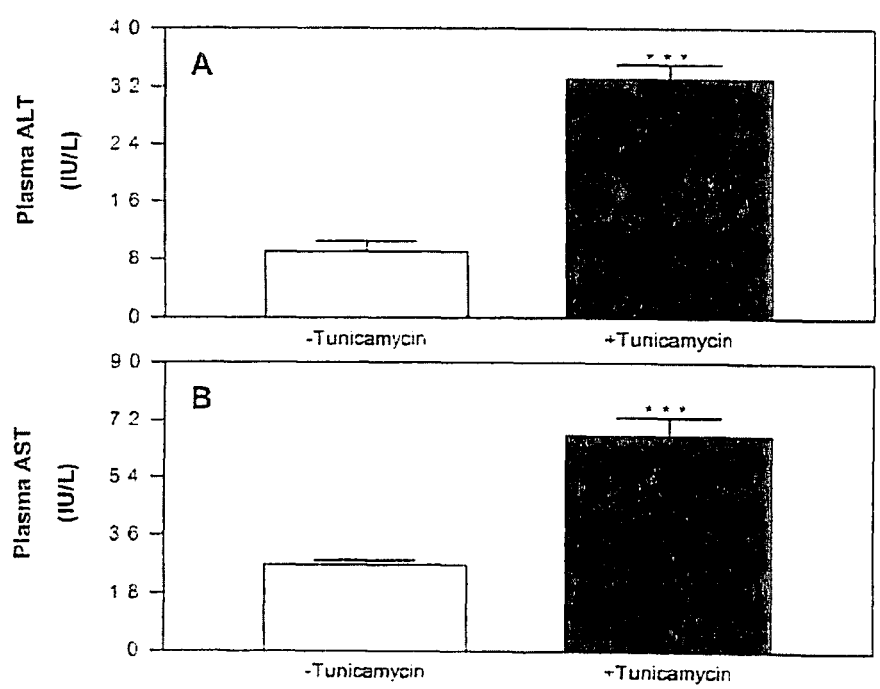
FIG. 10. Effect of tunicamycin on plasma ALT/AST levels. W iid type mice were injected intraperitoneally with 1 mg/kg tunicamycin. Plasma were collected after 48 h and used to measure enzyme activities.

To determine whether ER stress itself would increase plasma AST/ALT, C57Bl/6J mice were injected with tunicamycin (1 mg/kg) as described before. Plasma AST/ALT levels were measured after 36 h (FIG. 10). These enzymes were significantly enhanced in plasma indicating that ER stress augments their release. We will be measuring cellular lipid to determine whether tunicamycin affects hepatic lipid levels as well as mRNA and protein levels of different candidate genes involved in ER stress pathway.

The above experiments show that MTP ablation or its inhibition in mice and hepatoma cells increases cellular triglyceride, total and free cholesterol, Ire1α mRNA, and plasma/media AST/ALT levels. Cellular free cholesterol is decreased after treating with lovastatin and T-0901317 but not with WY14647. Peritoneal injections of Ω-3 FA (PPARα/PPARγ agonists) decreased both free cholesterol and triglyceride, and reduced plasma AST/ALT levels (data not shown). We, therefore, hypothesize that MTP ablation/inhibition leads to free cholesterol accumulation. In the absence of apoB-lipoprotein assembly and secretion this free cholesterol cannot be removed from ER. Thereafter, increases in free cholesterol induce ER stress leading to enhanced release of AST/ALT from liver cells. The buildup of hepatic free cholesterol can be avoided by inhibiting cholesterol synthesis using lovastatin or enhancing free cholesterol efflux/bile acid secretion by LXR agonists. Reduction in cellular free cholesterol diminishes Ire1α mRNA and reduces release of AST/ALT. Therefore; toxicities associated with MTP inhibition can be avoided by reducing cellular free cholesterol and triglyceride. These hypotheses will be tested in this proposal.

As stated above, MTP inhibitors have long been regarded as a possible alternative to the widely used statins due to their ability to target lipoprotein assembly. However, adverse effects in the liver i.e., tissue accumulation of lipids and elevations in plasma AST/ALT, have kept them from becoming a mainstay treatment for hyperlipidemia. Triglyceride and cholesterol, in particular free cholesterol, accumulation and subsequent plasma AST/ALT elevations are the hallmark adverse effects in the liver. The magnitude of the lipid-accumulation typifies hepatosteatosis, a growing public health concern due to its link to steatohepatitis and possibly cirrhosis. The studies discussed below focused on ameliorating the side effects associated with MTP inhibitors. To accomplish this, mice and monkeys treated with MTP inhibitors were also administered a combined PPARα/agonist (Picglitazone) or a statin (Lovastatin). PPAR α agonists act to increase p-oxidation of fatty acids, thereby metabolizing the accumulated triglycerides in the liver of MTP inhibitor treated animals. PPAR γ agonists also act to increase p-oxidation of fatty acids, but have the added property of promoting cholesterol efflux from hepatocytes. Statins are HMG-coA reductase inhibitors and therefore, block the endogenous synthesis of cholesterol. Statins, thereby, act to lower the accumulated cholesterol in hepatocytes. In both mice and monkeys, we observed a decrease in the accumulation of the appropriate lipids in the liver. The combined treatment of MTP inhibitor with a PPAR α/γ agonist prevented the accumulation of both triglycerides and cholesterol in the liver and curbed the elevations in plasma AST/ALT seen with the MTP inhibitor treatment alone. Similarly, statins curbed the rise in plasma AST/ALT but, only prevented the accumulation of cholesterol in the liver. The results of our studies advocate the use of a combination comprising at least one MTP inhibitor and at least one lipid lowering agent to treat the hyperlipidemias associated with metabolic diseases.

Additional experiments conducted confirm the conclusion that a combination of at least one Microsomal Triglyceride transfer Protein (MTP) inhibitor and at least one lipid lowering agent both in an amount effective to treat hyperlipidemias is effective in treating hyperlipidemias.

Example VI

Methods Used in the Additional Experiments Below

Animals: $Mttp^{tm2Sgy}$ $LdIr^{tm1Her}$ $Apob^{tm2Sgy}$ Tg(Mx1-cre)1Cgn/J mice (Reversa) (stock number 004192) were obtained from Jackson Laboratories. Male reversa mice were used to study the effect of mttp gene deletion on plasma and tissue lipids. These animals are transgenic for apolipoprotein B, $LDLR^{-/-}$ and floxed at exon 1 of the mttp locus. In addition, these mice express cre recombinase under the control of the Mx1 promoter, which is induced after intraperitoneal injection of polyinosinic polycytidylic ribonucleic acid (pIpC—Sigma) in the liver, spleen and intestine. Injection of pIpC activates the cre recombinase and deletes the mttp gene in the liver and intestines. Reversa mice were injected with either PBS or pIpC. Mice injected with pIpC were orally gavaged with DMSO (Sigma-Aldrich D8418), DMSO+Lovastatin (50 mg/kg/day) (Calbiochem 438186), DMSO+T0901317 (50 mg/kg/day) (Calbiochem 575310), or DMSO+WY14643 (10 mg/kg/day) (Calbiochem 681725). Mice injected with pIpC were also injected with either PBS or Ω-3 fatty acids (SUNY Downstate Medical Center). All animals were given supplemental treatments for 30 days.

C57BL/6J Black 6 mice (stock number 000664) were obtained from Jackson Laboratory and used for chow fed and western diet fed experiments. MTP inhibitor (BMS 2122122-01) (1 mg/kg/day), Lovastatin, Pioglitazone (Toronto Research Chemicals P471000) (25 mg/kg/day) and 4-phenylbutyric acid (Calbiochem 820986) (1 g/kg/day) were administered by oral gavage. Chow fed animals were treated for one week with either DMSO or MTP inhibitor. Western diet fed animals were fed DMSO, MTP inhibitor, Pioglitazone, MTP inhibitor+Pioglitazone, Lovastatin, MTP inhibitor+Lovastatin, 4-phenylbutyric acid, and MTP inhibitor+4-phenylbutyric acid. Chow fed animals were also injected with either PBS or Tunicamycin and animals were sacrificed at 4, 8, 12 and 24 hours.

Eleven (11) Male bonnet macaque monkeys were fed western diet for 40 days and treated with MTP inhibitor (BMS 2122122-01) with or without either Pioglitazone or Lovastatin for one month. Plasma samples were obtained at Day 0, 20, 40, 47, 54, 61 and 68 days. Liver biopsies were obtained on Day 40 and Day 68. Biopsies were conducted over two days; 2 animals from each group were biopsied per day.

All animals were kept in 07:00-19:00 h lighting schedule. All animals had free access to water and standard laboratory chow. Food was withdrawn 16 h before the sacrifice of the mice. On the day of the experiment, mice were anesthetized and blood was collected from the heart. Liver was collected, washed in ice-cold PBS, cut into small pieces and used for lipid extraction, histological staining, to measure different protein activities/quantities and for mRNA analysis. Lipids were extracted from the tissue homogenates following the Bligh and Dyer method. Triglyceride (Infinity TM Triglyceride, TR22421) and total cholesterol (Infinity TM Cholesterol, TR13421) levels in the tissues were determined using commercial kits (Thermo Scientific). Free cholesterol and free fatty acid levels were measured using kits from Wako Chemicals (Germany). Esterified cholesterol was calculated by subtracting the free cholesterol from the total cholesterol.

Determination of MTP Activity in Tissues:

After extensive washes with ice-cold PBS, small pieces (0.1 g) of liver and ~1-cm segments of proximal small intestine were homogenized with 1 ml of ice-cold 1 mM Tris-HCl, pH 7.6, 1 mM EGTA, and 1 mM $MgCl_2$ buffer in a glass homogenizer. The homogenates were centrifuged (SW55 Ti rotor, 50,000 rpm, 10° C., 1 h), and supernatants were used for MTP assay as described before (41; 42) using a kit (Chylos, Inc.).

mRNA quantifications and primers used: Total RNA from tissues and cells were isolated using TriZol™ (Invitrogen). The purity and integrity of RNA were assessed by the A260/A280 ratio and 1% agarose gel electrophoresis, respectively. Only the RNAs with ratios more than 1.7 were used for cDNA synthesis. The first strand cDNA was synthesized using Omniscript RT (Qiagen) kit. Briefly, 2 µg of total RNA, 1 µM random primers (Invitrogen), 0.5 mM dNTP solution, and 0.5 U/µl Omniscript Reverse Transcriptase were incubated at 37° C. for 1 h in 20 µl of RT buffer and the reaction was terminated by incubating at 95° C. for 5 minutes. Each reaction of quantitative RT-PCR was carried out in a volume of 20 µl consisting of 5 µl cDNA sample (1:100 dilution of the first strand cDNA sample) and 15 µl of PCR master mix solution containing 1×PCR reaction buffer, 6 mM $MgCl_2$, 200 nM primer pair, 0.025 U/µl HotStar Gold™ DNA polymerase, 200 µM dNTP solution, and 0.3 µl SYBR Green I solution (gPCR™ Core Kit for SYBR Green I, Eurogentec). The PCR was carried out by incubating the reaction mixture first for 10 minute at 95° C. followed by 40 cycles of 15 sec incubations at 95° C. and 1 min at 60° C. in the ABI 7000 SDS PCR machine. The data were analyzed using $\Delta\Delta C_T$-method according to manufacturer's instruction and presented as arbitrary units. The primers used in this study were designed with the PrimerExpress 3.0 software (Applied Biosystems, CA) and are presented as Table 1.

Figure 11:
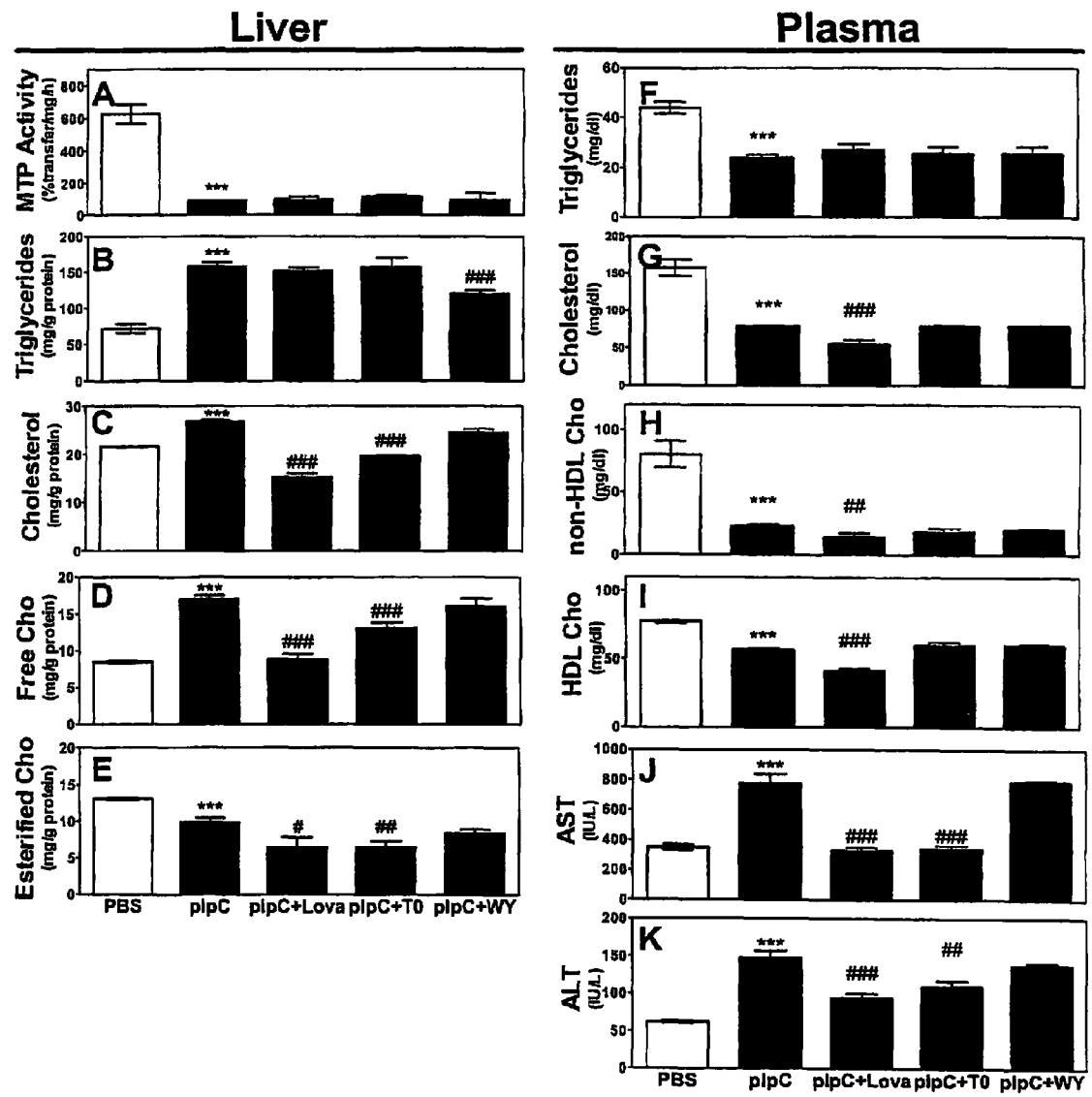
FIG. 11. Reversa animals were injected with plpC every other day for one week. Lovastatin, T-090317 and WY14643 were administered by oral gavage everyday for 30 days after the first injection. Animals were sacrificed on day 30 and plasma and livers were harvested and analyzed. * represent comparison to PBS injected animals and # represent comparisons to plpC control.

Statistical analyses: Data are presented as mean±S.D. Unless noted otherwise, n=3 for each group or condition. Statistical significance (P<0.05) was determined using the Student's t-test (GraphPad Prism).

terol (FIG. 11D) increased by 2-fold and 50%, respectively, in plpC-injected animals, whereas cholesteryl esters (CE) were reduced by ~30% (FIG. 11E) consistent with previous studies. Plasma total triglyceride (FIG. 11F) and cholesterol (FIG. 11G) were decreased by 50%. These reductions were mainly due to ~40% decrease in non-HDL-cholesterol (FIG. 11H). Plasma alanine aminotransferase (ALT) and aspartate aminotransferase (AST) were significantly increased (2-3 fold) in plpC-injected animals (FIGS. 11J-K). These studies show that mttp gene deletion enhances hepatic triglyceride and free cholesterol, reduces plasma triglyceride and cholesterol, and elevates plasma AST/ALT.

Lowering Hepatic Free Cholesterol Decreases Plasma AST/ALT in MTP Deficient Mice:

To determine whether accumulation of hepatic triglyceride and free cholesterol is related to increases in plasma AST/ALT, we sought to reduce these lipids using different chemical compounds of known physiologic effects. Mice injected with plpC were orally gavaged with DMSO, DMSO+Lovastatin (50 mg/kg/day), DMSO+T0901317 (50 mg/kg/day), or DMSO+WY14643 (10 mg/kg/day). Lovastatin (Lova), an HMG-CoA reductase (HMGR) inhibitor, and T0901317 (T0), an LXR agonist, are expected to decrease hepatic free cholesterol by inhibiting endogenous cholesterol synthesis and increasing cholesterol efflux, respectively. WY14643 (WY), a PPARα agonist, increases β-oxidation of fatty acids and lowers hepatic triglycerides. These compounds had no significant effect on the residual hepatic MTP activity in Reversa mice subjected to conditional mttp gene deletion (FIG. 11A). Lova and T0 had no effect, but WY reduced hepatic triglyceride (FIG. 11B). Lova and T0 significantly reduced free and total cholesterol, whereas WY had no effect on hepatic cholesterol (FIG. 11D). Analyses of plasma lipids showed that Lovastatin, T0, and WY had no effect on plasma triglycerides in MTP deficient mice (FIG. 11F). Lovastatin significantly reduced plasma cholesterol whereas T0 and WY had no effect (FIG. 11G). Lova and T0 significantly reduced plasma ALT/AST levels, while WY had no effect (FIGS. 11J-K). Therefore, lovastatin and T0 reduce hepatic free cholesterol and plasma transaminases whereas reductions in hepatic triglyceride by WY have no effect on these enzymes in MTP deficient mice. These studies indicate that reductions

TABLE 1 qPCR Primers

| Gene | 5' Primer | 3' Primer |
|------|-----------|-----------|
| Bip | CGG ACG CAC TTG GGA ATG AC | AAC CAC CTT GAA TGG CAA GAA |
| Ire1α | GCC CCG GGA GTT TTG G | GGG TCG AGA CAA ACA ACA AGG T |
| Perk | GGC AGG TCC TTG GTA ATC AT | CCA CTG CTT TTT CCC ATC AT |
| Atf-6 | GAC TGG GAG TCG ACG TTG TT | TCA TAA GCC TCA TGT GCT GG |
| Gapdh | GCA GTG GCA AAG TGG AGA TTG | GTG AGT GGA GTC ATA CTG GAA CAT G |

The primers listed were used to assay for ER stress markers in WDF mice treated with MTPi, MTPi + Pio or MTPi + Lo as described in FIGS. 2 and 3.

Mttp Gene Deletion Lowers Plasma and Tissue Lipids and Elevates Transaminases:

Male reversa mice were used to study the effect of mttp gene deletion on plasma and tissue lipids. Reversa mice were injected with either PBS or plpC. PipC treatment reduced hepatic MTP activity by ~75% compared to controls (FIG. 11A) indicating successful gene ablation. Analyses of lipids showed that hepatic triglyceride (FIG. 11B) and free cholesin hepatic free cholesterol accompany decreases in plasma transaminases in MTP deficient mice.

Since, WY treatment only modestly reduced hepatic triglycerides we sought a better method for their reduction and in determining their role in plasma AST/ALT elevations. In data not shown, we demonstrated that intraperitoneal injection of Ω-3 fatty acids (Ω-3 FA), an agonist for both PPARα and PPARγ, can significantly reduce hepatic triglycerides and free cholesterol. To avoid the necessity of injections, we searched for an oral agent with similar properties. Pioglitazone, a known agonist of PPARα and PPARγ, was selected to replace Ω-3 FA injections and was used for all subsequent experiments in animals.

Figure 12:
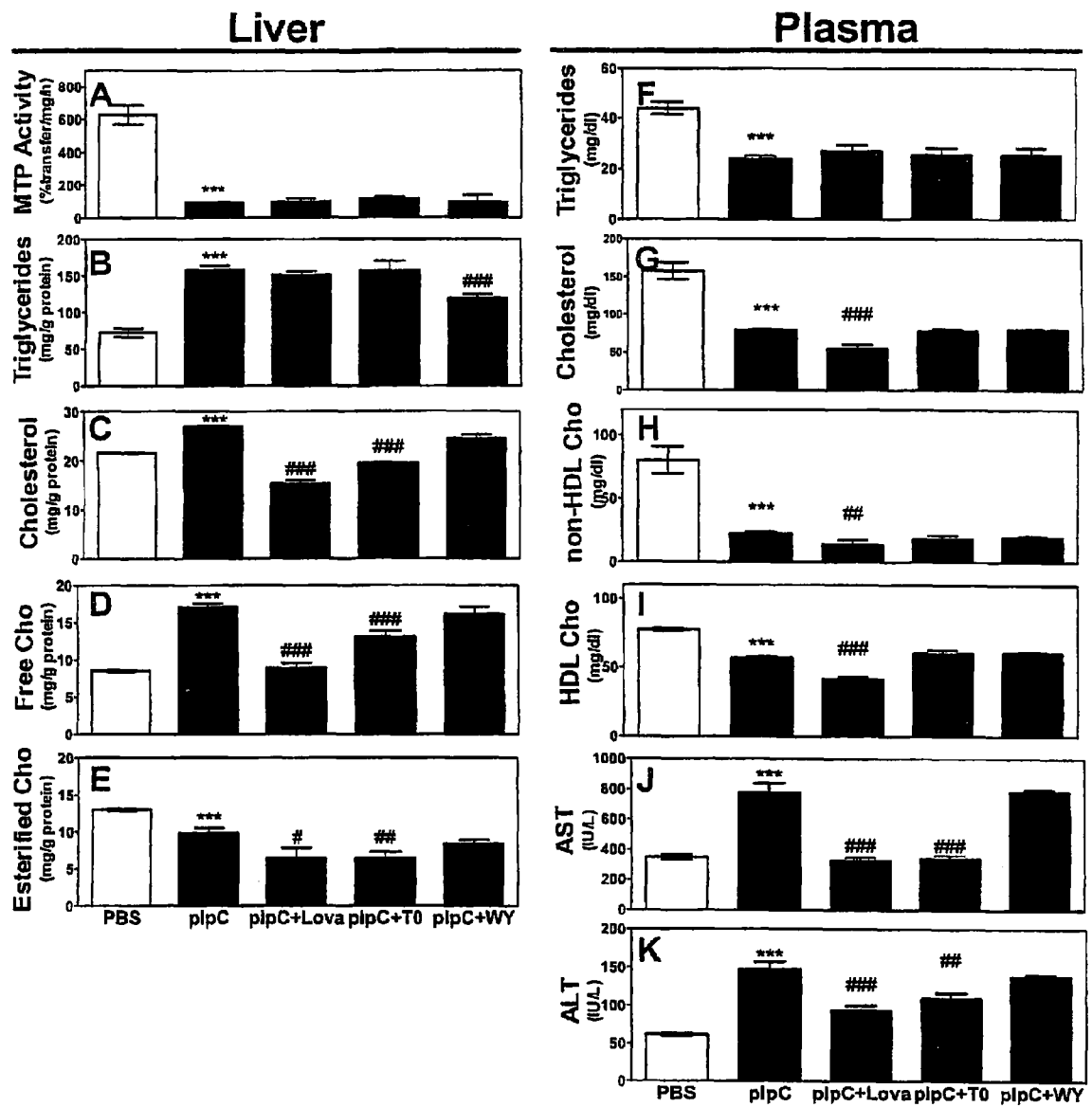
FIG. 12. plpC injected mice treated with intraperitoneal injection of Ω-3 FA (3 mg/kg/2 day) or Ω-3 FA and Lova were evaluated for the efficacy of Ω-3 FA in reducing hepatic triglyceride. These treatments had no effect on the residual MTP activity in mttp deficient animals (FIG. 12A). Ω-3 FA significantly reduced hepatic triglyceride (FIG. 12B). Surprisingly, Ω-3 FA also significantly reduced hepatic total cholesterol and FC (FIG. 12C), without altering cholesteryl esters (Suppl FIG. 12D).

Since, WY treatment only modestly reduced hepatic triglycerides we sought a better method for their reduction and in determining their role in plasma AST/ALT elevations. Ω-3 fatty acids (Ω-3 FA), an agonist for both PPARα and PPARγ, was selected based on triglyceride reduction capabilities (data not shown). To evaluate the efficacy of Ω-3 FA in reducing hepatic triglyceride, plpC injected mice were treated with intraperitoneal injection of Ω-3 FA (3 mg/kg/2 day) or Ω-3 FA and Lova. These treatments had no effect on the residual MTP activity in mttp deficient animals (FIG. 12A). Ω-3 FA significantly reduced hepatic triglyceride (FIG. 12B). Surprisingly, Ω-3 FA also significantly reduced hepatic total cholesterol and FC (FIG. 12C), without altering cholesteryl esters (Suppl FIG. 12D). Ω-3 FA and Lova further decreased hepatic total cholesterol and FC, but did not have any additional effects on hepatic triglycerides as compared to Ω-3 FA alone. Ω-3 FA did not alter plasma lipids (FIGS. 11B-C), but Ω-3 FA and Lova significantly reduced plasma triglyceride and cholesterol (FIGS. 15D-E). Ω-3 FA decreased plasma ALT/AST levels and this reduction was further augmented in the presence of Lova (FIGS. 11F-G). These studies indicate that a significant reduction of hepatic triglyceride and modest reduction in free cholesterol by Ω-3 FA can lower ALT/AST. When supplemented with Lova there is further reduction in hepatic free cholesterol and further reductions in plasma ALT/AST. These studies show that reductions in hepatic free cholesterol normalize plasma AST/ALT levels in mttp gene ablated mice.

Increases in Plasma ALT/AST Due to Chemical Inhibition of MTP can be Avoided by Reducing Hepatic Free Cholesterol In Vivo.

Figure 13:
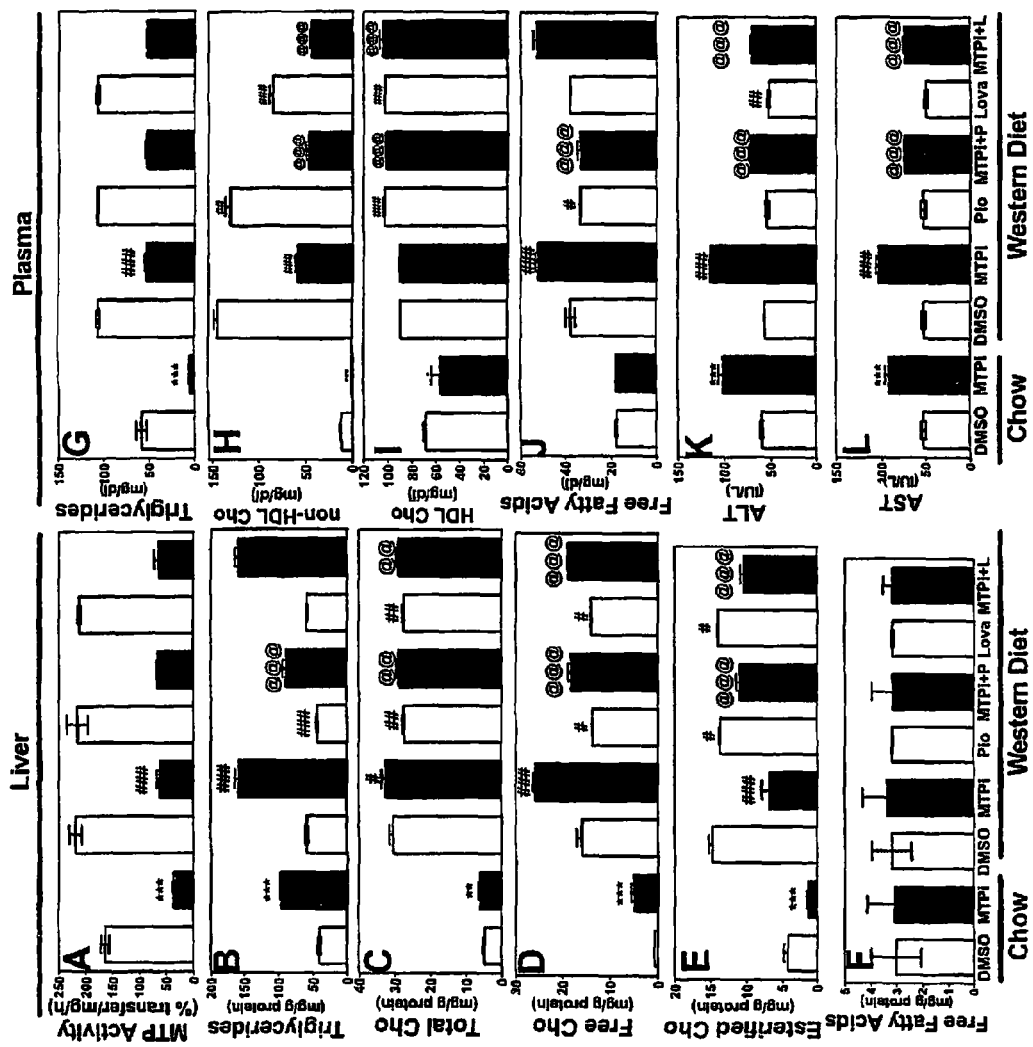
FIG. 13. Age matched wildtype C57/Bl6J animals chow fed animals were treated with DMSO (control) or MTP inhibitor (MTPi) for one week. Age matched wildtype C57/BL6J were fed WD for one month and were administered MTPi, Lovastatin, (Lovas) or Pioglitazone (Pio) everyday for one week. All drugs were administered by oral gavage. Animals were sacrificed on day 7 and plasma and livers were harvested and analyzed. * represent comparison to DMSO control; # represent comparisons to WD control; @ represent comparisons to WD MTP inhibitor treatment.

We next studied the effects of chemical inhibition of MTP in C57Bl/6J mice fed either a chow or western diet (WD) for 5 weeks. Chow fed animals were orally gavaged with either DMSO or MTP inhibitor BMS-212122-01 (MTPi; 1 mg/kg/day) for one week. WD fed animals were treated with DMSO, MTP inhibitor with or without lovastatin (50 mg/kg/day) or pioglitazone (25 mg/kg/day) daily by oral gavage for one week. As expected, treatment with MTPi significantly reduced MTP activity and was not further affected by lovastatin or pioglitazone (FIG. 13A). Lovastatin and pioglitazone alone had no effect on MTP specific activity (FIG. 13A). MTPi treatment significantly enhanced hepatic triglycerides, which was abrogated by pioglitazone treatment but not by lovastatin (FIG. 13B). Pioglitazone treatment alone had slightly lower hepatic triglycerides as compared to western diet fed controls, whereas lovastatin treatment alone had no effect on hepatic triglycerides (FIG. 13B). MTPi treatment also enhanced hepatic free cholesterol and this effect was reduced by the co-administration of lovastatin and pioglitazone (FIG. 13D). Pioglitazone and lovastatin treatment alone both decreased hepatic total and free cholesterol (FIGS. 13C-D). Hepatic free fatty acids (FFA) were not affected by MTP inhibition and these levels were resistant to lovastatin and pioglitazone therapies (FIG. 13F). Similar to mttp deficient mice, MTPi treated mice had significantly lower plasma triglyceride and cholesterol (FIGS. 13G-H). Plasma FFA levels, however, did increase upon high fat feeding and MTPi treatment but, was completely abrogated by pioglitazone treatment (FIG. 13J). On the other hand, MTPi plus lovastatin treatment had no effect on the elevated plasma FFA seen with high fat feeding and MTP inhibitor treatment (FIG. 13J), suggesting that elevations in plasma FFA is not likely to be the cause of enhanced release of AST/ALT upon MTPi treatment. Treatment with lovastatin and pioglitazone alone had no effect on plasma lipids (FIGS. 13G-J). MTPi treatment significantly enhanced plasma ALT/AST levels (FIGS. 13K-L) correlating with the rise in hepatic free cholesterol. The addition of lovastatin to MTPi treatment lowered plasma AST/ALT providing further evidence that free cholesterol accumulation in the livers of MTP deficient animals promotes hepatic AST/ALT release. However, pioglitazone lowers both triglyceride and free cholesterol and might be more beneficial than lovastatin as combination therapy with MTPi to lower plasma lipids and avoid increases in hepatic lipids and plasma transaminases.

Besides the liver, MTP is also expressed in the intestine and heart. Therefore, we also studied changes in lipids in these tissues following MTP inhibition and co-administration of lovastatin and pioglitazone. As in the liver, accumulation of triglycerides and free cholesterol ensued in the intestine (Table 2). Furthermore, administration of pioglitazone in conjunction with MTPi attenuated the rise in intestinal free cholesterol seen with MTPi alone (Table 1). As expected, lovastatin had no effect on intestinal lipids (Table 1). Cardiac tissue exhibited no changes in lipid profiles with MTPi or MTPi+pioglitazone or lovastatin treatment (Table 2).

TABLE 2

Intestinal and cardiac lipids in western diet fed MTPi treated mice.
C57BL/6J mice were fed a western diet for 30 days and then administered DMSO (Control), MTPi, MTPi + Pio or MTPi + Lo as described in FIG. 2.
Intestines and hearts were collected and lipid extractions were performed to identify any changes in lipid homeostasis.

| Tissue | Control | MTPi | MTPi + Pio | MTPi + Lo |
|---|---|---|---|---|
| Intestine (mg/g protein) | | | | |
| Triglycerides | 364.705 ± 27.3 | 711.534 ± 113.2*** | 346.479 ± 35.3### | 642.817 ± 99.4*** |
| Cholesterol | 41.528 ± 1.4 | 60.342 ± 8.6** | 35.945 ± 10.4## | 57.97 ± 3.8** |
| Free Cholesterol | 22.865 ± 0.9 | 48.814 ± 10.6*** | 20.173 ± 6.4### | 46.472 ± 1.3*** |
| Free Fatty Acids | 0.745 ± 0.0 | 0.648 ± 0.1 | 0.724 ± 0.1 | 0.633 ± 0.1 |
| Heart (mg/g protein) | | | | |
| Triglycerides | 146.474 ± 28.9 | 134.044 ± 41.6 | 152.695 ± 19.3 | 130.713 ± 28.8 |
| Cholesterol | 21.665 ± 1.2 | 24.617 ± 4.2 | 23.61 ± 2.6 | 20.182 3.2 |

TABLE 2-continued

Intestinal and cardiac lipids in western diet fed MTPi treated mice.
C57BL/6J mice were fed a western diet for 30 days and then administered
DMSO (Control), MTPi, MTPi + Pio or MTPi + Lo as described in FIG. 2.
Intestines and hearts were collected and lipid extractions were performed to
identify any changes in lipid homeostasis.

| Tissue | Control | MTPi | MTPi + Pio | MTPi + Lo |
|---|---|---|---|---|
| Free Cholesterol | 12.068 ± 0.8 | 13.495 ± 2.4 | 12.559 ± 1.4 | 10.488 ± 2.2 |
| Free Fatty Acids | 0.916 ± 0.1 | 0.746 ± 0.1 | 0.868 ± 0.1 | 0.945 ± 0.2 |

Comparisons with Control animals are designated with *.
Comparisons with MTPi treated animals are designated with #.
Values are mean ± SD.
*,#p < 0.05;
**,##p < 0.01;
***,###p < 0.001;
n = 4 per group.

Figure 14:
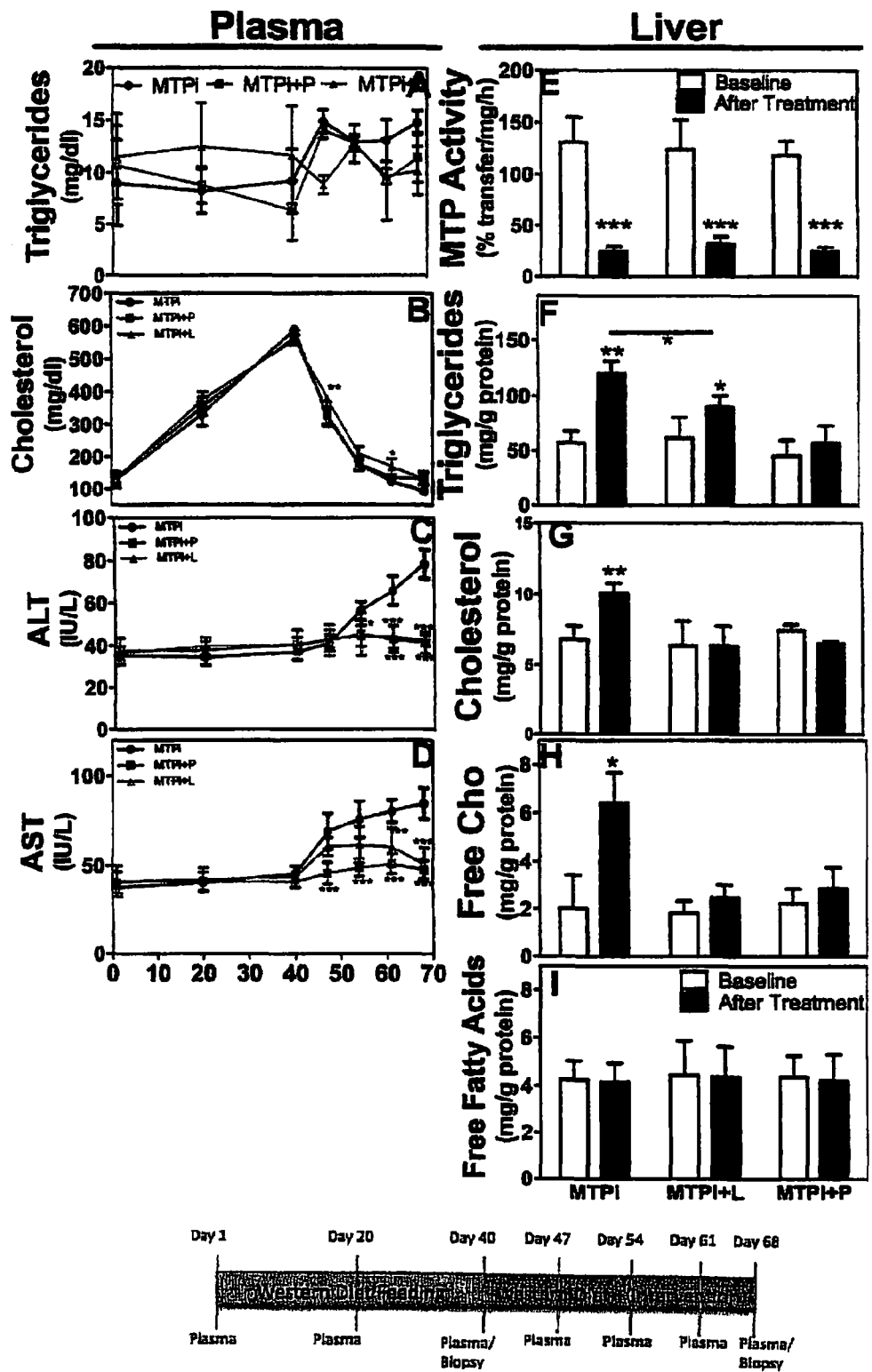
FIG. 14. Bonnet Macaque monkeys fed ad libitum WD diet for 40 days and were administered MTPi, Lovastatin, (Lovas) or Pioglitazone (Pio) everyday for one month. A-D* represent comparisons to the MTPi alone group. E-I* represent comparisons between baseline and post biopsies.

In order to ascertain if the effects seen were a species-specific effect, we studied the treatment of MTP inhibitors either alone or in conjunction with Pioglitazone or Lovastatin in hyperlipidemic bonnet macaques. These animals were fed ad libitum with a WD for 40 days and then subsequently treated with MTP inhibitors for one month. There were no significant differences in fasting plasma triglycerides in the three groups at the start of the trial, after 40 days of western diet or after treatment suggesting that neither the diet or drug intervention had any significant effect on fasting plasma triglycerides (FIG. 14A). However, feeding of WD significantly increased plasma cholesterol on day 20 and this increase continued until day 40 (FIG. 14B). Again, there were no significant differences in plasma cholesterol in these groups. MTP inhibitor sharply reduced plasma cholesterol in the first week and this decline continued until 3 weeks; thereafter no further reduction was seen on the $4^{th}$ week (FIG. 14B). Administration of Pioglitazone or Lovastatin had no further significant effect on the reduction of plasma cholesterol (FIG. 14B). These studies indicate that western diet increases plasma cholesterol and that these increases can be abrogated by treatment with an MTP inhibitor.

Plasma AST/ALT levels increased slightly after feeding WD for 40 days; however, they were not significantly different from baseline levels (FIGS. 14C-D). MTP inhibitor treatment significantly increased plasma AST levels and these levels remained elevated through week 4 (FIG. 14D). Plasma ALT levels were also significantly elevated upon MTPi treatment during weeks 3 and 4. Similarly, monkeys fed MTP inhibitor and Lovastatin had high levels of AST, however this increase subsided by week 3 (FIG. 14D). In contrast, monkeys that received MTP inhibitor and Pioglitazone did not show any significant differences in AST/ALT levels from baseline and day 40, indicating that Pioglitazone provided protection against MTP inhibitor induced increases in plasma AST/ALT (FIGS. 14C-D).

Hepatic triglycerides rose significantly upon treatment with MTP inhibitor (FIG. 14E). Similarly, MTP inhibitor treatment with Lovastatin also demonstrated significantly elevated levels of hepatic triglycerides (FIG. 14E). In contrast, Pioglitazone treatment showed no significant difference in hepatic triglycerides from the onset of treatment (FIG. 14E). Hepatic cholesterol, total and free, increased upon treatment with MTP inhibitor and this increase was suppressed upon additional treatment of both pioglitazone and lovastatin (FIG. 14F, 14I). Furthermore, free fatty acid levels were not significantly different from the onset of treatment in all groups (FIG. 14H). These studies indicate that pioglitazone treatment in conjunction with MTP inhibitors can abrogate the tissue specific side effects seen with MTP inhibitor treatment.

Figure 15:
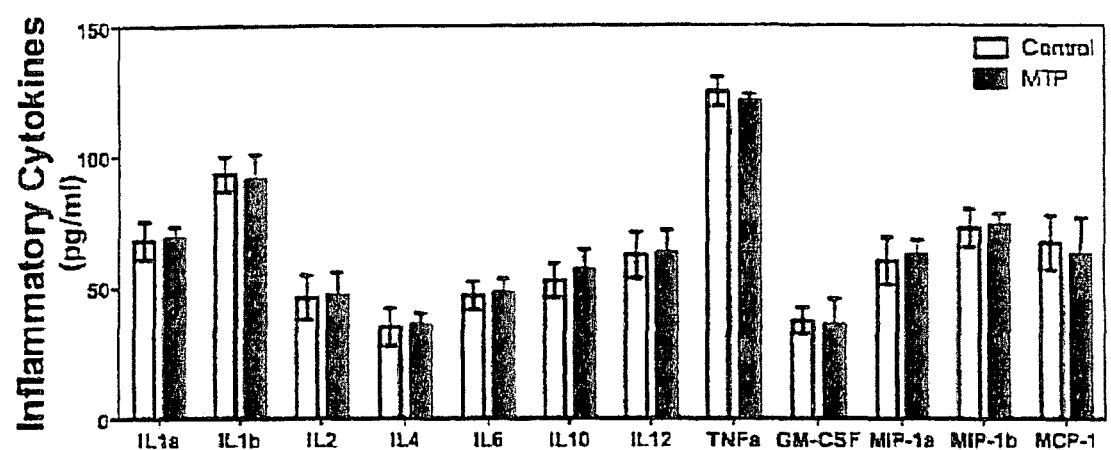
FIG. 15 is a graph showing no significant differences in various cytokines in the plasma of control and MTP inhibitor treated mice excluding inflammation as a cause for the release of AST/ALT.
Figure 16:
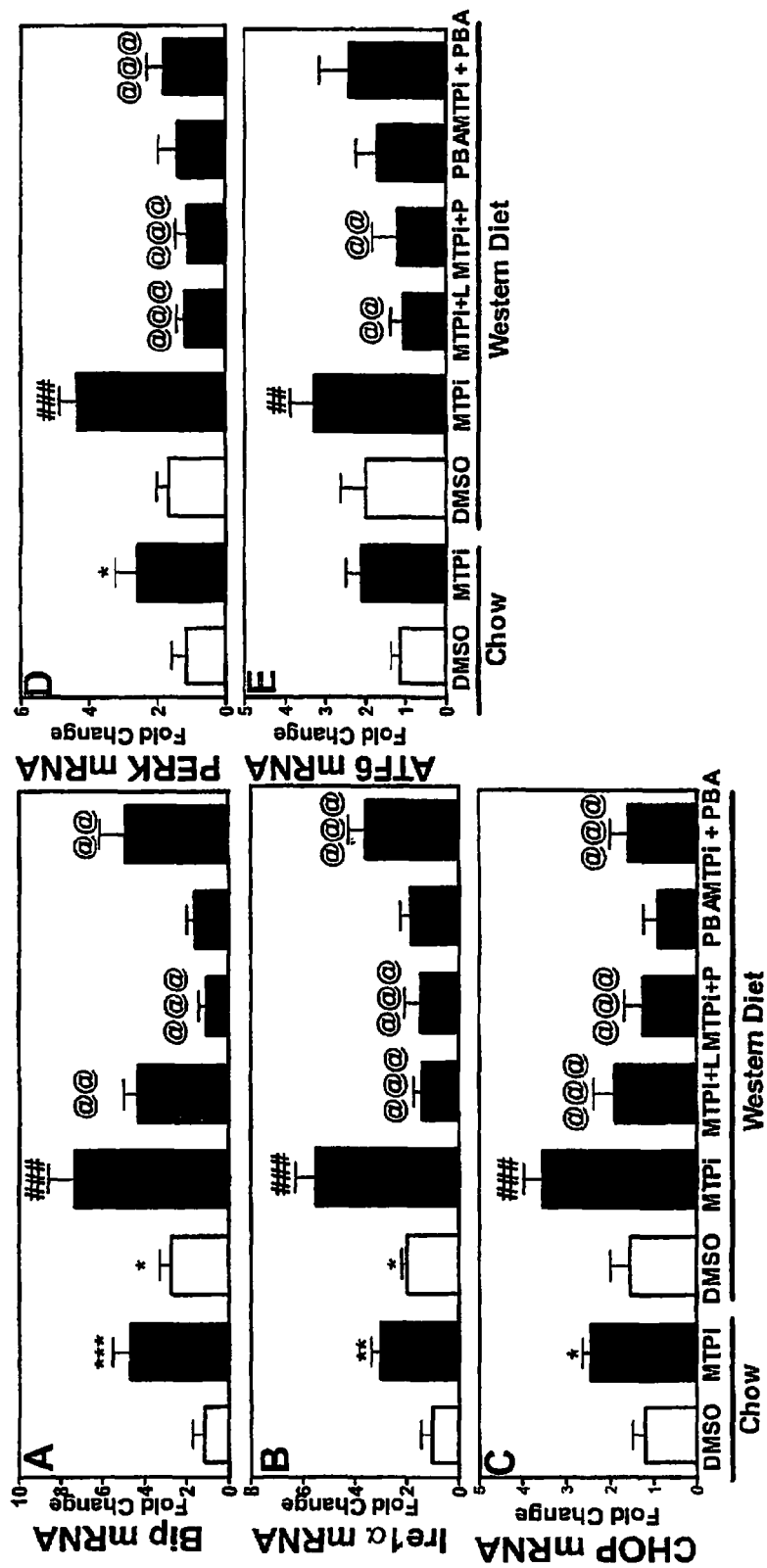
FIG. 16. Age matched wildtype C57/BL6J animals chow fed animals were treated with DMSO (control) or MTP inhibitor (MTPi) for one week. Age matched wildtype C57/BL6J were fed WD for one month and were administered MTPi, Lovastatin, (Lova), Pioglitazone (Pio) or 4-phenylbutyric acid (PBA) every day for one week. All drugs were administered by oral gavage. Animals were sacrificed on day 7 and livers were harvested. mRNA was extracted and subjected to qPCR analysis. * represent comparison DMSO control; # represent comparisons to WD control; @ represent comparisons to WD MTP inhibitor treated animals.

Induction of ER Stress Increases Plasma AST/ALT After MTP Inhibition:

Attempts were then made to identify mechanisms that lead to the release of AST/ALT after MTP inhibition. There were no significant differences in various cytokines in the plasma of control and MTP inhibitor treated mice excluding inflammation as a cause for the release of AST/ALT (FIG. 15). Free cholesterol loading induces ER stress in macrophages and therefore we sought to elucidate whether the same response could be seen in the livers of MTP deficient animals. We therefore measured changes in mRNA levels of Bip, Ire1α, CHOP, PERK and ATF6, general markers of the ER stress response. Bip, Ire1α, CHOP, PERK and ATF6 mRNA levels increased in MTPi treated animals and were significantly lower after lovastatin and pioglitazone treatment suggesting curbing of the ER stress response (FIGS. 16A-E). These studies indicate that MTP inhibition might cause ER stress.

Figure 17:
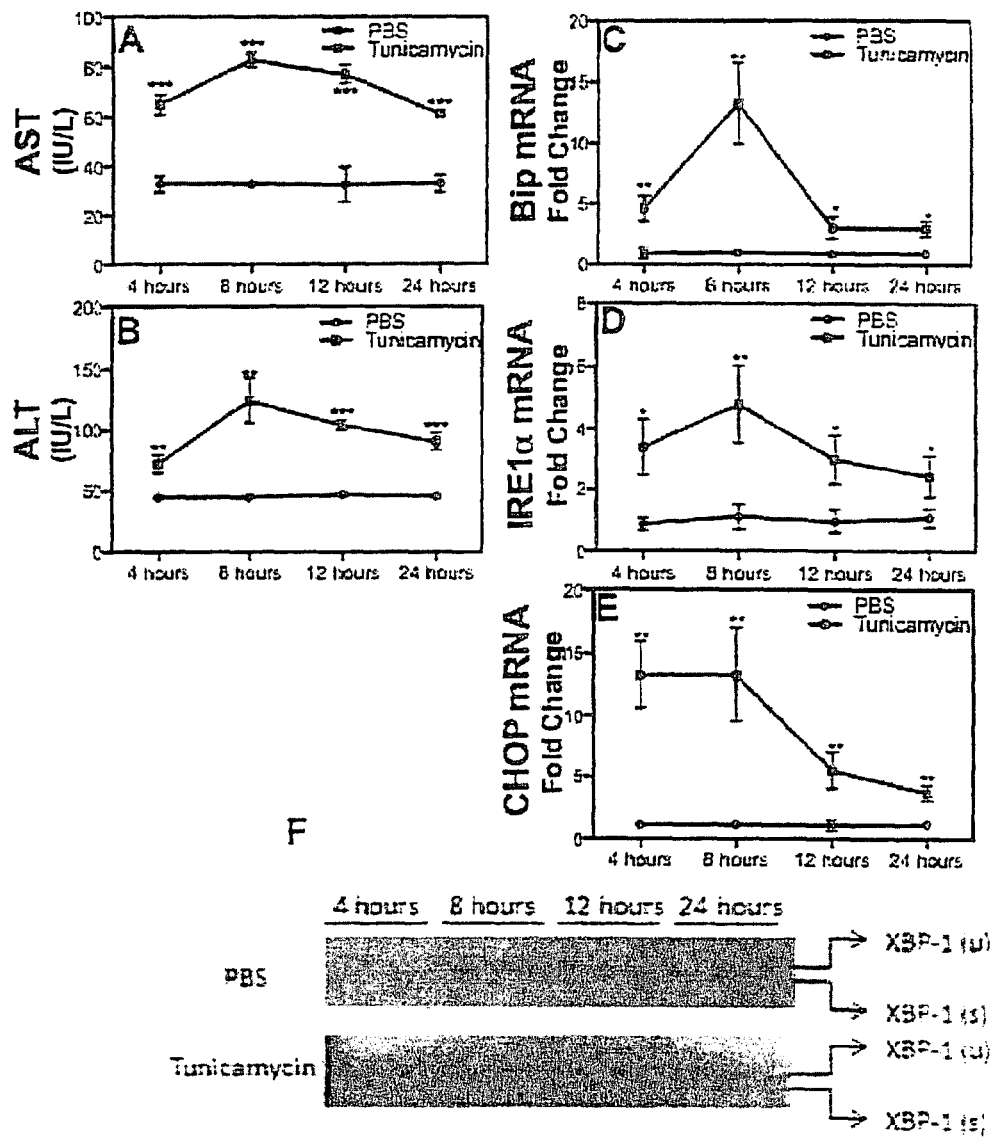
FIG. 17. Age matched wildtype C57/BL6J animals chow fed animals were injected via IP with either PBS or Tunicamycin. Animals were sacrificed at 4, 8, 12 and 24 hours. Plasma and livers were collected and mRNA extracted from liver samples.

To establish further that ER stress enhances plasma AST/ALT, normal C57/BL6J were treated with tunicamycin for different time points. Tunicamycin had no effect on hepatic MTP activity, lowered plasma cholesterol and triglycerides and increased hepatic lipids (FIGS. 15A-D). These mice had higher plasma transaminases indicating ER stress increases plasma transaminases. Plasma AST/ALT levels peaked 8 hours after tunicamycin injection, and began to subside thereafter (FIGS. 17A-B). However, 24 hours after injection plasma AST/ALT were still significantly elevated from PBS injected animals. mRNA expression of ER stress markers revealed elevations in Bip, Ire1α and CHOP (FIGS. 17C-E). XBP-1 splicing assay also revealed the spliced form of XBP-1 indicating induction of ER stress with Tunicamycin injection (FIG. 15F). Furthermore, PBS injected animals showed no spliced variant of XBP-1 suggesting the absence of ER stress in these animals (FIG. 17F).

Figure 18:
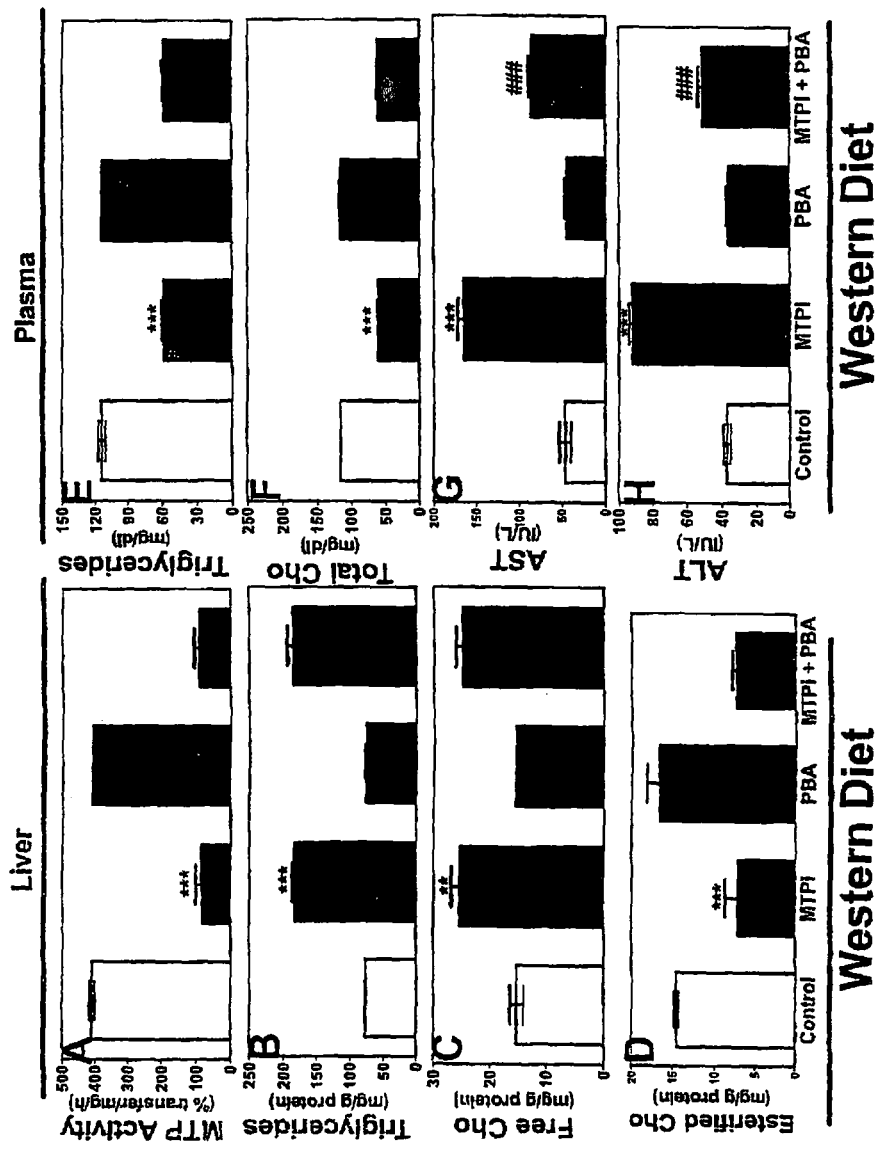
FIG. 18. Age matched wildtype C57/BL6J were fed WD for one month and were administered MTPi, or 4-phenylbutyric acid (PBA) everyday for one week. All drugs were administered by oral gavage. Animals were sacrificed on day 7 and livers were harvested. * represent comparison DMSO control; # represent comparisons to HF MTP inhibitor treated animals.

To examine whether ER stress is involved in the release of AST/ALT in MTP deficient models, animals treated with MTP inhibitor were co-treated mice with an ER stress inhibitor, 4-phenyl-butyric acid (PBA). Treatment of mice with MTP inhibitors reduced MTP activity (FIG. 18A); reduced plasma lipids (FIGS. 18E-F); and increased hepatic triglycerides and free cholesterol (FIGS. 18B-C). In contrast, PBA had no effect on these parameters (FIGS. 18A-H). Co-administration of MTP inhibitor and PBA had no effect on MTP activity, hepatic and plasma lipids (FIGS. 18A-F). However, it abrogated rises in plasma AST/ALT (FIGS. 18G-H). These studies indicate that ER stress plays a role the release of AST/ALT after MTP inhibition. Furthermore, mRNA levels of ER stress markers in PBA treated animals were significantly lower than MTPi treated animals suggesting curbing of the ER stress response by PBA (FIGS. 18A-E). These studies indicate that ER stress plays a role the release of AST/ALT after MTP inhibition.

Reports of AST/ALT elevations in MTP deficient models have been varied. In a clinical trial of Familial Hypercholesterolemia (FH) patients treated with MTP inhibitors, increases in both plasma aminotransferases and hepatic fat in four out of the six patients were reported. Samaha et al described, in a clinical trial of MTP inhibitor+Ezetimibe (intestinal cholesterol absorption inhibitor) treated hyperlipidemic patients, that nine of the fifty-six patients had elevations of ALT/AST at least 2 times the upper limit of the normal range. In a review by Joy and Hegele, it was suggested that MTP deficiency associated hepatic fat accumulation might be correlated with AST/ALT elevations. In case studies of patients with ABL (or Familal Hypobetalipoproteinemia (mutation in apolipoprotein B) it has been reported that a majority of patients had significantly increased hepatic fat and plasma AST/ALT. As varied as reports have been in human studies, so has it been in animal models. In one mouse model it was suggested that MTP deficiency sensitizes the liver to toxin mediated injury and alone has no effect on plasma AST/ALT. However, in another model of MTP deficiency plasma AST/ALT elevations were seen in female rats at higher doses and were correlated with increased hepatic fat]. Despite the varied reports of plasma AST/ALT elevations in MTP deficient models, one consistency seems to be that elevations in plasma AST/ALT are associated with elevations in hepatic fat content. This may be a reflection of the differential capacities of the liver to accommodate lipid accumulation. Furthermore, in many of the clinical trials studying MTP inhibitors individual basal AST/ALT levels were never compared to post-treatment AST/ALT levels. In all trials elevations were reported as factor X times the upper limit of the normal ranges of these enzymes. Therefore, it is entirely plausible that AST/ALT levels may be within normal ranges or slightly above normal ranges and still is elevated when compared to individual basal levels.

The studies presented here provide evidence that MTP gene ablation and its chemical inhibition decreases plasma non-HDL triglyceride and cholesterol as well as hepatic cholesteryl esters; elevates hepatic triglyceride and free cholesterol; and enhances plasma AST and ALT levels. Reductions in non-HDL lipids can be explained by the well-known role of MTP in the assembly and secretion of triglyceride-rich apoB-containing lipoproteins. Reductions in hepatic cholesteryl esters are consistent with the studies of Iqbal et al who showed that MTP plays a regulatory role in their biosynthesis. They showed that MTP removes cholesteryl esters and relieves product inhibition. Therefore, in the absence of MTP activity cholesterol ester biosynthesis is curtailed leading to accumulation of free cholesterol in the liver. Increases in hepatic triglyceride can be explained by the inhibition of apoB-lipoprotein biosynthesis. Similarly, free cholesterol accumulation can be secondary to inhibition of cholesteryl ester biosynthesis. Data presented here provides evidence that these increases might be secondary to accumulation of free cholesterol.

To try and alleviate the burden of hepatic lipid accumulation, we co-administered either cholesterol or triglyceride lowering drugs with genetic ablation or chemical inhibition of MTP. Lovastatin, an HMGR inhibitor, and T-0901317, a LXR agonist, treatment in cells or animals without functional MTP resulted in a decrease in accumulated cellular free cholesterol and more importantly, a depressed rise in plasma ALT/AST. Conversely, treatment with triglyceride lowering drugs, such as WY14643, a PPARα agonist, lowered cellular triglycerides but had no effect free cholesterol levels and the rise in plasma transaminases. It was only when a cholesterol lowering agent was supplemented with a triglyceride lowering treatment, or when treatment involved a single agent with triglyceride and cholesterol lowering properties, such as Ω-3 fatty acids or Pioglitazone (combined PPARα/γ agonists), did a triglyceride lowering agent have an effect on plasma ALT/AST. Collectively this data provides compelling evidence that reductions in free cholesterol can abrogate the changes in plasma ALT/AST seen in MTP deficient models.

Genetic expression of endoplasmic reticulum stress effectors was also elevated in MTP deficient models, suggesting that the accumulation of free cholesterol in the liver induces stress in the ER. The role of ER stress in toxicities associated with MTP deficiency has not been fully elucidated. Liao et al reported that genetic ablation and chemical inhibition of MTP interferes with apoB secretion without causing retention or stress in the ER. However, when considering the massive lipid accumulation in the liver with MTP inhibition and the role free cholesterol plays in the induction of ER stress in arterial wall macrophages, it does not seem plausible that ER stress plays no role in MTP inhibitor associated toxicities. ER stress has been implicated in numerous models of hepatic lipid perturbations. Collision et al reports that high fructose corn syrup leads to elevations in hepatic cellular triglycerides and elevations in ER stress markers. In a review by Kaplowitz et al, it is suggested that there is sufficient evidence for an important role of the endoplasmic reticulum (ER) stress response in the pathogenesis of chronic viral hepatitis, insulin resistance and nonalcoholic fatty liver disease, genetic disorders of protein malfolding, and alcoholic liver disease. Basseri et al and Lee and Glimcher, both implicate intersections between the ER stress pathway and hepatic lipid metabolism. Lee and Glimcher, go as far to suggest that it is unlikely that ER stress is not active in a model of MTP deficiency and owes the inability of its recognition to inadequate means of assaying for ER stress. Furthermore, we demonstrate that ER stress induced by Tunicamycin can result in the release of these enzymes into the plasma. More importantly, we demonstrate that by inhibiting ER stress with the molecular chaperone PBA, we can curb the ER stress response and the rise in plasma AST/ALT seen with MTP inhibition.

MTP has been a target of therapeutic intervention for almost 20 years. Several pharmaceutical companies have heavily invested in identifying MTP antagonists to lower plasma cholesterol levels. However, therapeutic use of all currently developed compounds results in elevated plasma transaminases and hepatic lipid accumulation. As a consequence, MTP antagonists are only used for limited purposes, such as, lowering lipids in patients with familial hypercholesterolemia or controlling obesity in dogs. It is also currently being evaluated as a possible alternative to bariatric surgery to control blatant obesity, and liver transplantation to lower hyperlipidemias in familial hypercholesterolemia. The idea that hepatic toxicities associated with MTP inhibition are due to free cholesterol is novel. These studies introduce a new concept for avoiding the side effects associated with MTP antagonists and advocates novel combinatorial approaches to treat hyperlipidemias and lead to new therapeutic modalities for the treatment of various hyperlipidemias and have immediate potential for translational use.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A combination consisting of at least one Microsomal Triglyceride transfer Protein (MTP) inhibitor and at least one lipid lowering agent, both in an amount effective to treat hyperlipidemias.

2. The combination of claim 1 wherein said at least one lipid lowering agent is a PPARα/PPARγ agonist or statin.

3. The combination of claim 2 wherein the PPARα/PPARγ agonist is (RS)-5-(4-[2-(5-ethylpyridin-2-yl)ethoxy]benzyl) thiazolidine-2,4-dione.

4. The combination of claim 2 wherein the statin is 1S,3R, 7S,8S,8aR)-8-{2-[(2R,4R)-4-hydroxy-6-oxooxan-2-yl] ethyl}-3,7-dimethyl-1,2,3,7,8,8a-hexahydronaphthalen-1-yl (2S)-2-methylbutanoate.

5. A method of treating hyperlipidemias in a subject, said method comprising administering the combination of claim 1 to said subject.

6. A method of treating hyperlipidemias in a subject, said method comprising administering the combination of claim 2 to said subject.

7. A method of treating hyperlipidemias in a subject, said method comprising administering the combination of claim 3 to said subject.

8. The method of claim 5 wherein the MTP inhibitor is administered in an amount of about 50-100 mg per day and the lipid-lowering agent is administered in an amount of about 50-100 mg per day.

9. The method of claim 5 wherein the MTP inhibitor and the lipid lowering agent are administered together as a pharmaceutical composition or as part of the same, unitary dosage form.

10. The method of claim 5 wherein the MTP inhibitor and the lipid lowering agent are administered separately, but as part of the same therapeutic regimen.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: artificial sequence
<220> FEATURE:
<223> OTHER INFORMATION: 5' PCR primer to mouse Bip gene

<400> SEQUENCE: 1
cggacgcact tgggaatgac                                          20

<210> SEQ ID NO 2
<211> LENGTH: 16
<212> TYPE: DNA
<213> ORGANISM: artificial sequence
<220> FEATURE:
<223> OTHER INFORMATION: 5' PCR primer to mouse Ire1 alpha gene

<400> SEQUENCE: 2
gccccgggag ttttgg                                              16

<210> SEQ ID NO 3
<211> LENGTH: 20
<212> TYPE: DNA
<213> ORGANISM: artificial sequence
<220> FEATURE:
<223> OTHER INFORMATION: 5' PCR primer to mouse Perk gene

<400> SEQUENCE: 3
ggcaggtcct tggtaatcat                                          20

<210> SEQ ID NO 4
<211> LENGTH: 20
<212> TYPE: DNA
<213> ORGANISM: artificial sequence
<220> FEATURE:
<223> OTHER INFORMATION: 5' PCR primer to mouse Atf-6 gene

<400> SEQUENCE: 4
gactgggagt cgacgttgtt                                          20

<210> SEQ ID NO 5
<211> LENGTH: 21
<212> TYPE: DNA
<213> ORGANISM: artificial sequence
<220> FEATURE:
<223> OTHER INFORMATION: 5' PCR primer to mouse Gapdh gene

<400> SEQUENCE: 5
gcagtggcaa agtggagatt g                                        21

<210> SEQ ID NO 6
<211> LENGTH: 21
<212> TYPE: DNA
<213> ORGANISM: artificial sequence
<220> FEATURE:
<223> OTHER INFORMATION: 3' PCR primer to mouse Bip gene

<400> SEQUENCE: 6
aaccaccttg aatggcaaga a                                        21
```

```
<210> SEQ ID NO 7
<211> LENGTH: 22
<212> TYPE: DNA
<213> ORGANISM: artificial sequece
<220> FEATURE:
<223> OTHER INFORMATION: 3' PCR primer to mouse Ire1 alpha gene

<400> SEQUENCE: 7
gggtcgagac aaacaacaaggt                                             22

<210> SEQ ID NO 8
<211> LENGTH: 20
<212> TYPE: DNA
<213> ORGANISM: artificial sequence
<220> FEATURE:
<223> OTHER INFORMATION: 3' PCR primer to mouse Perk gene

<400> SEQUENCE: 8
ccactgcttt ttcccatcat                                               20

<210> SEQ ID NO 9
<211> LENGTH: 20
<212> TYPE: DNA
<213> ORGANISM: artificial sequence
<220> FEATURE:
<223> OTHER INFORMATION: 3' PCR primer to mouse Atf-6 gene

<400> SEQUENCE: 9
tcataagcct catgtgctgg                                               20

<210> SEQ ID NO 10
<211> LENGTH: 25
<212> TYPE: DNA
<213> ORGANISM: artificial sequence
<220> FEATURE:
<223> OTHER INFORMATION: 3' PCR primer to mouse Gapdh gene

<400> SEQUENCE: 10
gtgagtggag tcatactgga acatg                                         25
```